United States Patent
Haggblom et al.

(12)

(10) Patent No.: US 6,905,864 B2
(45) Date of Patent: Jun. 14, 2005

(54) PAENIBACILLUS NAPHTHALENOVORANS THAT DEGRADES NAPHTHALENE

(75) Inventors: Max M. Haggblom, New York, NY (US); Lori Daane, Los Alamos, NM (US)

(73) Assignee: Rutgers, the State University, New Brunswick, NJ (US)

( * ) Notice: Subject to any disclaimer, the term of this patent is extended or adjusted under 35 U.S.C. 154(b) by 319 days.

(21) Appl. No.: 10/156,562

(22) Filed: May 24, 2002

(65) Prior Publication Data

US 2003/0100098 A1 May 29, 2003

Related U.S. Application Data

(62) Division of application No. 09/375,932, filed on Aug. 17, 1999, now Pat. No. 6,503,746.
(60) Provisional application No. 60/096,769, filed on Aug. 17, 1998.

(51) Int. Cl.[7] .................................................. C12N 1/20
(52) U.S. Cl. ................................ 435/252.1; 435/252.4; 435/252.5; 435/262.5; 424/93.46; 424/93.3
(58) Field of Search .......................... 435/252.4, 252.5, 435/252.1, 262.5; 424/93.46, 93.3

(56) References Cited

PUBLICATIONS

Meyer et al., Microbiology (Reading, United Kingdom) (Jul. 1999), 145(7), 1731–1741.*
Ash et al., "Molecular Identification of rRNA Group 3 Bacilli(Ash, Farrow, Wallbanks and Collins) Using a PCR Probe Test", 1993 Antonie van Leewenhoek 64:253–260.
Pichinoty et al., "Bacillus gordonae sp. nov., une Nouvelle Espéce Appartenant au Second Groupe Morphologique, Dégradant Divers Composés Aromatiques", Ann. Inst. Pasteur/Microbiol. 1986 137A:65–78.
Heydrickx et al., *Paenibacillus* (Formerly *Bacillus*) *gordonae* (Pichinotiv et al. 1986) Ash et al. 1994 is a Later Subjective Synonum of *Paenibacillus* (Formerly *Bacillus*) *validus* (Nakamura 1984) Ash et al., 1994:Emended Descripton of P. validus. International Journal of Systemic Bacteriology 45:661–669.

* cited by examiner

*Primary Examiner*—Irene Marx
(74) *Attorney, Agent, or Firm*—Licata & Tyrrell P.C.

(57) ABSTRACT

Polyaromatic hydrocarbons are found in contaminated soils and groundwater and are a large class of compounds for which treatment by bioremediation is sought. Accordingly, indigenous organisms that can degrade polyaromatic hydrocarbon are needed. Presented are strains of the *Paenibacillus* genus that degrade low molecule weight polyaromatic, and, in the presence of phenanthrene, high molecular weight polyaromatic hydrocarbons. These bacteria strains are unique among PAH-degrading bacterial strains because they form endospores and therefore can survive adverse environmental conditions. Among the strains presented are several from "*P. naphthalenovorans*", a newly described species. Also presented are compositions for bioremediation comprising the bacterial strains of the invention, and a method for isolating the strains and a method for using the strains for bioremediation.

9 Claims, 7 Drawing Sheets

PAENIBACILLUS NAPHTHALENOVORANS THAT DEGRADES NAPHTHALENE

This application is a Divisional Application of U.S. Ser. No. 09/375,932, filed Aug. 17, 1999 now U.S. Pat. No. 6,503,746 which claims the benefit of priority from Provisional Application 60/096,769, filed Aug. 17, 1998, which is incorporated in its entirety by reference herein.

FIELD OF THE INVENTION

This invention relates to the field of bacterial strains used for bioremediation. In particular, it relates to endospore-forming bacterial strains that can degrade polyaromatic hydrocarbons, and methods to isolated these bacterial strains and to use these strains for bioremediation.

BACKGROUND OF THE INVENTION

Various scientific and scholarly articles are referred to throughout the specification. These articles are incorporated by reference herein to describe the state of the art to which this invention pertains.

Polyaromatic hydrocarbons (PAHs) are widespread pollutants, particularly in conjunction with the marine environment. High PAH levels are known to be toxic, mutagenic and carcinogenic, and therefore pose a considerable threat to the public health. Many microorganisms degrade PAHs, and there is a strong interest in applying bioremediation approaches to remove PAHs from the environment.

Bacteria that degrade 2–3 ring low molecular weight polyaromatic hydrocarbons, such as naphthalene, phenanthrene, bi-phenyl and fluorene, are taxonimically diverse. Gram negative genera such as *Pseudomonas, Burkholderia, Alcaligens, Sphingomonas, Vibrio* and *Comamonas* are common. While less common, the gram-positive species such as *Mycobacterium, Nocardia, Rhodococcus* and *Gordona* are also known to degrade low molecular weight PAHs.

Microorganisms that can degrade the 4-ring and higher high molecular weight PAHs such as pyrene, fluoranthene and benz[a]anthracene are much rarer. The degradation of high molecular weight PAHs is much slower and less extensive than the degradation of low molecular weight PAHs in the environment.

The isolation of new genera of PAH-degrading bacteria is sought, particularly species with novel combinations of growth and degradative characteristics. In particular, species are sought with a broad range of PAH specificities. Species that can degrade the higher molecular weight PAHs are particularly valuable. Finally, PAH-degrading species that are capable to surviving adverse nutritional and environmental conditions by forming endospores are of particular interest.

SUMMARY OF THE INVENTION

The invention pertains to isolated strains of bacteria that degrade polyaromatic hydrocarbons, a method of isolating the strains of the invention and a method of using the strains of the invention for bioremediation. The bacterial strains are in the family Bacillaceae and are novel for their combination of PAH-degrading and endospore-forming properties. These bacterial strains have utility for bioremediation of polyaromatic hydrocarbon in contaminated environments.

The first aspect of the invention is an isolated strain in the family Bacillaceae that has broad PAH-degrading capabilities in that it degrades at least two of the PAHs naphthalene, phenanthrene and biphenyl. In a preferred embodiment, the strain additionally degrades pyrene when induced by phenanthrene. Preferably, the strain is in the isolate *Paenibacillus*, and most preferably in the species *P. validus*. This isolated bacterial strain may be isolates PR-PR1, PR-N4 and PR-B2, which are ATCC Accession Nos. PTA-643, PTA-642 and PTA-641 respectively.

The second aspect of the invention is an isolated bacterial strain that is the newly described species "*Paenibacillus naphthalenovorans*" and degrades naphthalene. This bacterial strain is further described by several features. The strain has, in a preferred embodiment, a whole cell fatty acid composition in which 16:1 ω11c fatty acids comprise at least 8.8%, and additionally, in a most preferred embodiment, at least 5.8% but not more than 10.0% 17:0 anteiso fatty acids, when grown on trypticase soy agar at 28° C. for 24 hours prior to analysis. In another preferred embodiment, the isolated strain has a whole cell fatty acid similarity index as compared to isolate PR-N1 of greater than 0.4 when grown on trypticase soy agar at 28° C. for 24 hours prior to analysis. In another preferred embodiment, the bacterial strain has a 16SrRNA gene sequence that is at least about 95% homologous to SEQ ID NO:8. In another preferred embodiment, the genomic DNA of the strain exhibits at least 10% binding to the genomic DNA of isolate PR-N1. In another preferred embodiment, the strain is ATCC Accession No. PTA-640.

Another aspect of the invention is a plurality of bacterial strains that degrade PAHs. This plurality comprises at least two of the following: *Paenibacillus validus*, a sphingomonad, an Arthrobacter, "*Paenibacillus naphthalenovorans*" and a nocardioform. In a preferred embodiment, the *P. validus* strain is ATCC Accession No. PTA-641, PTA-642 or PTA-643 and the "*P. naphthalenovorans*" and a nocardioform. In a preferred embodiment, the *P. naphthalenovorans* strain is ATCC Accession No. PTA-640. Strain deposits were made at the American Type Tissue Culture Collection at 10801 University Boulevard, Manassas, Va. 20110-2209 on Sep. 10, 1999.

Another aspect of the invention is a composition for bioremediation that comprises one of the aforementioned bacterial strains and an ecologically acceptable carrier.

Another aspect of the invention is a method for removing PAHs from a substrate comprising contacting the substrate with the bacterial strain of the invention for a time sufficient to remove the PAHs. In preferred embodiments, the substrate of the method is solid or liquid, with optional aeration. In a more preferred embodiment, the method additionally comprises planting plants in the substrate, and in a most preferred embodiment, the plant is *Spartina alterniflora*. In another most preferred embodiment, the method has the additional step of inducing of the bacterial strain with phenanthrene.

Another aspect of the invention is a method to isolate endospore-forming PAH-degrading bacterial strains. This method comprises the steps of growing a heterogenous culture with a PAH as the sole carbon source, and heating the culture to a temperature for a time sufficient to kill vegetative bacteria. In preferred embodiments, the PAHs used are naphthalene, phenanthrene or biphenyl. In another preferred embodiment, the culture is heated to 70 to 90° C. for 10 to 20 minutes.

Other features and advantages of the present invention will be better understood by reference to the drawings, detailed description and examples that follow.

DETAILED DESCRIPTION OF THE INVENTION

I. Definitions

Figure 1:
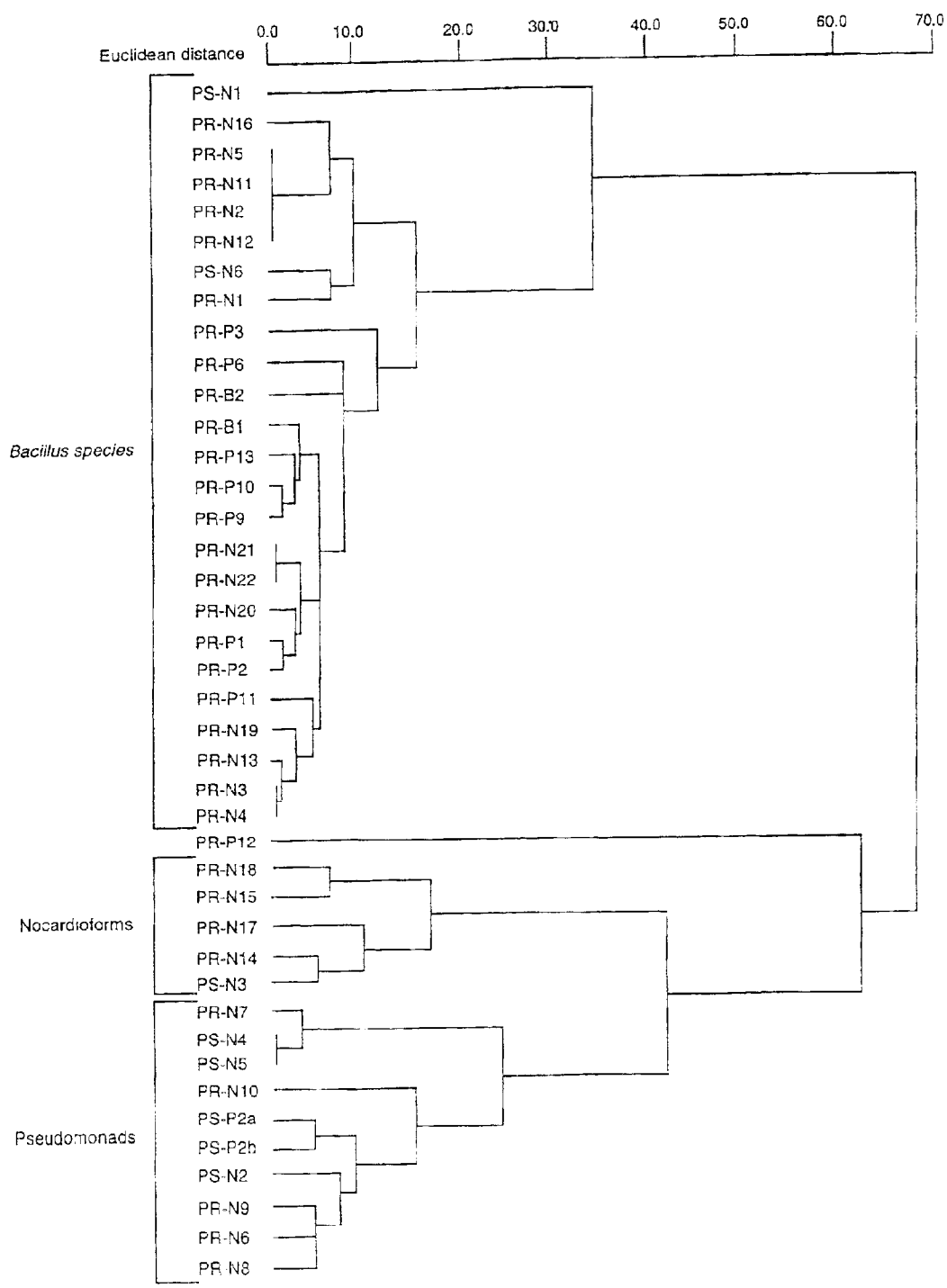
FIG. 1. Euclidean distance dendrogram based on the whole-cell fatty acid compositions of all the PAH-degrading strains isolated by enrichment from sediment and rhizosphere samples obtained from Lewes, Del. and Piles Creek, N.J. The aerobic (TSBA) library version 3.9 of the Microbial Identification System (MIDI Inc, Newark, Del.) was used to perform a comparative analysis.

Various terms relating to the biological molecules used to describe the present invention are used hereinabove and also throughout the specification and claims.

With reference to nucleic acids, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a prokaryote or eukaryote. An "isolated nucleic acid molecule" may also comprise a cDNA molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

The term "substantially pure" refers to a preparation comprising at least 50–60% by weight the compound of interest (e.g., nucleic acid, oligonucleotide, protein, etc.). More preferably, the preparation comprises at least 75% by weight, and most preferably 90–99% by weight, the compound of interest. Purity is measured by methods appropriate for the compound of interest (e.g. chromatographic methods, agarose or polyacrylamide gel electrophoresis, HPLC analysis, and the like).

With respect to single stranded nucleic acid molecules, the term "specifically hybridizing" refers to the association between two single-stranded nucleic acid molecules of sufficiently complementary sequence to permit such hybridization under predetermined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "substantially the same" refers to nucleic acid or amino acid sequences having sequence variation that do not materially affect the nature of the protein (i.e. the structure, stability characteristics and/or biological activity of the protein). With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure or function.

The terms "percent identical" and "percent homologous" are also used herein in comparisons among nucleic acid sequences. "Percent identical" and "percent homologous" refers to the percent of the nucleotides of the subject nucleic-acid sequence that have been matched to identical nucleotides by a sequence analysis program. With respect to the present invention, the percent identity of nucleic acid sequences is determined by the PILEUP program in the Genetics Computer Group (GCG) software package using the default parameters II. Description Provided with the present invention are two species of bacteria that have useful properties for bioremediation, and methods to isolate and use these species for bioremediation. The two bacteria species have been found to be able to degrade polycyclic aromatic hydrocarbons. This ability makes these two species very useful for the bioremediation of soils and waters contaminated with polycyclic aromatic hydrocarbons (PAHs). These bacterial species also possess the useful ability to form endospores in order to survive adverse conditions. The first species, *Paenibacillus validus*, has the ability to degrade a broad spectrum of low molecular weight PAHs, including naphthalene, phenanthrene, bi-phenyl, p-hydroxybenzoate and benzoate, as well as the higher molecular weight PAHs such as pyrene and fluoranthene when induced by phenanthrene. This species was not previously known to degrade such a broad range of PAHs.

The second species, tentatively named "*Paenibacillus naphthalenovorans*", is a PAH-degrading species heretofore unidentified. Provided herein are characteristics such as whole cell fatty acid composition, rRNA gene sequence and phenotypic characteristics that define "*Paenibacillus naphthalenovorans*" as a novel species. In conjunction with its initial description herein is the discovery that this new species degrades naphthalene and m-hydroxybenzoate and is useful for bioremediation.

Also provided is a method to use these two bacterial species to treat contaminated sediment, soil or water, as well as a method to isolate endospore-forming bacterial strains that degrade PAHs.

In accordance with the present invention, rhizosphere soil samples and sediment samples were collected from salt marshes and an estuary in Delaware and New Jersey. These site were categorized as pristine or contaminated with PAHs. The bacterial populations from these samples were enriched for PAH-degrading species by growth on naphthalene, phenanthrene or biphenyl as the sole carbon source (Example 1). Isolated strains were morphologically and phenotypically characterized and compared to type strains using phase-contrast microscopy, whole cell fatty acid profiles and assorted biochemical tests standard in bacterial identification. Heat treatment was used to screen for endospore-forming gram-positive bacteria that would have useful survival properties. The use of heat treatment in conjunction with the isolation of PAH-degrading bacteria is novel and specifically isolates endospore-forming bacteria the degrade PAHs.

The resulting isolates were categorized as gram-negative or gram-positive. Tentative identification based on whole cell fatty acid composition led to assignments of genus to the isolates (Tables 2–4). Several gram-negative bacterial species were isolated, mostly from the genus *Pseudomonas* but also from *Alcaligenes* and *Flavobacterium*. The gram-positive isolates mainly fell into the genera of *Paenibacillus, Nocardia, Mycobacterium* and *Arthrobacter*. None of the strains tested was particularly effective at metabolizing pyrene, while all could metabolize naphthalene with high efficiency, and biphenyl, fluorene and phenanthrene with varying degrees of efficiency.

The "*Bacillus*" isolates were all from the genus *Paenibacillus*. The discovery of *Paenibacillus* isolates that could degrade PAHs, and particularly phenanthrene, is novel. These species of bacteria are very desirable for bioremediation efforts because of their ability to form endospores during times of nutrient limitation or adverse environmental conditions. These endospores can remain dormant for many years and retain the ability to germinate and form vegetative cells. The ability to form endospores gives these bacteria a longevity and stability in the environment not found in other bacteria.

The *Paenibacillus* isolates were characterized further with whole cell fatty acid analyses, phenotypic characteristics, G+C content, rRNA gene sequence and DNA binding experiments (Ash et al., 1993, Antonie Van Leeuwenhoek, 64:253–260; incorporated by reference herein). 16S rRNA gene phylogenetic analysis and fatty acid analysis determined that the isolates were members of the genus *Paenibacillus* with a high percent of 15:0 anteiso, 15:0 iso, 16:0 iso, 17:0 iso and 17:0 anteiso fatty acids typical of the genus *Paenibacillus* (Table 6).

Colony morphology divided the isolates into two groups, mucoid and nonmucoid. When used in accordance with the bacterial species of the present invention, mucoid morphology is defined as producing slimy colonies on tryptic soy agar. The amount of 10:0 iso, 16:1 ω11c and 16:0 fatty acids also distinguished between these two groups (Table 6), as does partial rRNA gene sequence analysis. While both groups have rRNA gene sequences with significant homology to the *P. validus* rRNA gene, the nonmucoid group has higher homologies, 95–98%, than the mucoid group, 93–95%. Fatty acid analysis and rRNA gene sequences determined that the nonmucoid *Paenibacillus* isolates were from the known species *P. validus*, while the mucoid colony isolates were from a novel species. This novel species has been tentatively named "*Paenibacillus naphthalenovorans*".

Further differences were found in phenotypic characteristics of the isolates of the two groups in the Voges-Proskauer test and esculin hydrolysis; and the ability to produce acid from glycerol, ribose, D-xylose, dulcitol, inositol, amidon and glycogen (Table 8). The two groups also differed in their ability to grow-on aromatic substrates (Table 9). The nonmucoid *P. validus* isolates metabolized a wider range of aromatic substrates including naphthalene, phenanthrene, biphenyl, p-hydroxybenzoate and benzoate, but not m-hydroxybenzoate. The mucoid "*P. naphthalenovorans*" isolates can grow on naphthalene, p-hydroxybenzoate, benzoate and m-hydroxybenzoate, but not phenanthrene and biphenyl. When induced by phenanthrene, *P. validus* strain PR-P1 was found to degrade the high molecule weight PAHs pyrene and fluoranthrene.

*Paenibacillus validus* (Pichinoty et al., 1986, Ann. Inst. Pastuer/Microbiol. 137A:65–78; Nakamura et al., 1984, Int. J. Sys. Bacteriol. 34:410–413; both are incorporated by reference herein) is an established species, and as such there are established characteristics that may be used to identify strains of this species. This species is now defined to encompass the species *Paenibacillus gordonae* (formerly *Bacillus gordonae*) (Heyndrickx et al., 1995, Int. J. Sys. Bacteriol. 45:661–669; incorporated by reference herein). Defining species characteristics include similarity to the *P. validus* type strain (ATCC Accession No. 43897). Such defining characteristics are well known in the art and include similarity of 16S rRNA gene sequence, whole cell fatty acid profile and phenotypic characteristics.

In accordance with the invention, isolates of *P. validus* have been discovered that will grow with the low molecular weight PAHs phenanthrene and biphenyl as the sole carbon source. Of the PAHs naphthalene, phenanthrene and biphenyl, the isolated bacterial strain of the invention will grow on at least two in a preferred embodiment, and all three in a most preferred embodiment.

Also in accordance with the present invention it is now known that *P. validus* isolates will degrade the high molecular weight PAHs fluoranthene and pyrene when induced by phenanthrene. The ability of bacteria to degrade these high molecular weight is very rare and these compounds therefore persist in the sediment. It is contemplated that the metabolic stimulation by phenanthrene will also occur in many Bacillaceae species.

Example 3 contains the description of several PAH-degrading isolates of *P. validus*. Isolates PR-P1, PR-N4 and PR-B2 have been deposited with the American Type Culture Collection as accession numbers PTA-643, PTA-642 and PTA-641. Taught herein are the whole cell fatty acid profiles of 14 isolates (Table 6), the phenotypic characteristics of 6 isolates (Table 8), the 16S rRNA gene sequences of 5 isolates (SEQ ID NOs:1–5), the mole percent G+C of 4 isolates (Table 10), and percent genomic DNA binding for 2 isolates (Table 10) and the PAH-degrading properties of 3 isolates (Table 9). It is contemplated that by teaching the characteristics of this group of isolates, that the isolated bacterial strain of the invention includes all PAH-degrading strains isolated in the species *P. validus*.

*Paenibacillus validus* is the first known species in the Bacillaceae that is able to degrade a wide variety of PAHs. The Bacillaceae contain species of gram positive, motile, rod-shaped bacteria that form endospores. Given the highly related nature of bacteria in this group, it is very likely other genera of the group will also contain members with PAH-degrading capabilities. It is therefore contemplated that the isolation of several PAH-degrading strains in the family Bacillaceae will lead to the isolation of many more from all the genera. The isolated bacterial strain of the invention is therefore contemplated to encompass all species that metabolize PAHs in addition to naphthalene in the family Bacillaceae. In a preferred embodiment, the isolated bacterial strain is in the genus *Paenibacillus* (Ash et al., 1993, Antonie van Leeuwenhoek 64:253–260; Shida et al., 1997, Int. J. Sys. Bacteriol. 47:289–298; all are incorporated by reference herein). In the most preferred embodiments, the bacterial strain is *P. validus*.

The second isolated bacterial strain of the invention is in the newly discovered species, "*Paenibacillus naphthalenovorans*". Isolate PR-N1 has been deposited in the American Type Culture Collection as representative of this new species (ATCC Accession No. PTA-640.

In accordance with the present invention, the first isolation of "*P. naphthalenovorans*" strains are taught in Example 1, and a use for these strains in bioremediation is taught in Example 3. It is therefore contemplated that another aspect of the instant invention is an isolated bacterial strain that is an isolated strain of "*P. naphthalenovorans*".

In accordance with the present invention, "*Paenibacillus naphthalenovorans*" is defined by the characteristics traditionally used in the art to define bacterial species: 16S rRNA gene sequence, percent genomic DNA binding, whole cell fatty acid profiles and phenotypic characteristics. Methods to obtain these characteristics and apply them to taxonomically define a bacterial species is well known in the art. In accordance with the present invention, definitive characteristics of 6 PAH-degrading isolates of "*P. naphthalenovorans*" are taught, and the invention is therefore contemplated to encompass all PAH-degrading isolates in the species "*P. naphthalenovorans*".

The 16S rRNA gene is also an excellent indicator of genealogical relationship between species and is the most non-changing genetic marker available. The 16S ribosome gene sequences of six "*P. naphthalenovorans*" isolates are taught in accordance with the present invention (SEQ ID NOs:6–11). In respect to the current invention, the sequence for PR-N1 16S rRNA gene sequence (SEQ ID NO:8) is used as the type sequence for this new species. The percent homology of the 16S rRNA gene sequence for the "*P. naphthalenovorans*" of the invention to SEQ ID NO:8 is greater than about 95% in a preferred embodiment, greater than about 96% in a more preferred embodiment, and greater than about 97% in a most preferred embodiment. With respect to the present invention, the percent identity of 16S rRNA gene sequences is determined by the PILEUP program in the Genetics Computer Group (GCG) software package using the default parameters over the approximately 500 bp fragment generated by 27f and 1522r PCR primers.

Another way to characterize a species is through the general homology found in the genomic DNA. The percent binding (or hybridization) of one genomic DNA sample to another will give a quantitative measure of the homology between the two genomes. In regard to the current invention, the method used to determine these homologies is the S1 nuclease method (Johnson, 1994, In Methods for General and Molecular Bacteriology, pp 655–682, Gerhardt, Murry, Wood and Kreig (eds.), Washington D.C., American Society of Microbiology), and the "*P. naphthalenovorans*" type genome is the PR-N1 genome (ATCC Accession No. PTA-640). The percent DNA binding of the "*P. naphthalenovorans*" of the invention to the "*P. naphthalenovorans*" type genome is at least 15% in a preferred embodiment, at least 40% in a more preferred embodiment, and at least 70% in a most preferred embodiment.

Fatty acid identification has been proven very useful in identifying organisms on the genus and species levels. It is a form of chemotaxonomy, and it characterizes the number and diversity of complicated biosynthetic pathways that a species possesses. By comparing the whole cell fatty acid composition of an unknown bacterium to the fatty acid compositions of type stains, the most like species of the unknown bacterium is determined. In order for these comparisons to have meaning, both all the bacteria must be grown under similar conditions. In regards to the current invention, standard growth conditions for whole cell fatty acid analysis are growth on trypticase soy agar at 28° C. for 24 hours prior to analysis. Comparisons of the fatty acids profiles are now done by computer programs with databases. Regarding the isolated bacterial cultures of the present invention, the Sherlock Microbial Identification System (Operating Manual Version 5, from MIDI, Inc., Newark, Del.) are used. A similarly index provides the degree of identity to the type strain in the MIDI library database or library databases constructed with MIDI software, with 1.0 being a perfect match. The similarity index of the "*P. naphthalenovorans*" of the invention to the whole cell fatty acid composition of isolate PR-N1 (Table 6) is greater than 0.4 in a preferred embodiment, greater than 0.6 in a more preferred embodiment, and greater than 0.6 in the most preferred embodiment.

The percentages of individual fatty acids may also identify a species of bacteria. A predominance of the fatty acid 15:0 anteiso is characteristic of *Paenibacillus* (Ash-et al., 1993, Antonie van Leeuwenhoek 64:253–260). The higher levels of 16:1 ω11c and moderate levels 17:0 anteiso fatty acids are characteristic of "*Paenibacillus naphthalenovorans*". The preferred embodiments of each individual fatty acid of the species "*P. naphthalenovorans*" are indicated in Table 1.

TABLE 1

Preferred embodiments of the percent whole cell fatty acid for each fatty acid of the "*Paenibacillus naphthalenovorans*". "X" is the percent of the whole cell fatty acids on a w/w basis of the isolated "*P. naphthalenovorans*" of the invention.

| Fatty Acid | Preferred | More Preferred | Most Preferred |
|---|---|---|---|
| 14:0 iso | $0.0\% \leq X \leq 3.0\%$ | $0.0\% \leq X \leq 2.5\%$ | $0.0\% \leq X \leq 2.3\%$ |
| 14:0 | $2.5\% \leq X$ | $2.5\% \leq X \leq 6.0\%$ | $2.5\% \leq X \leq 3.7\%$ |
| 15:0 iso | $4.7\% \leq X \leq 10.0\%$ | $3.0\% \leq X \leq 6.8\%$ | $4.7\% \leq X \leq 6.8\%$ |
| 15:0 anteiso | $35\% \leq X$ | $45\% \leq X$ | $45\% \leq X \leq 55\%$ |
| 15:0 | $0.0\% \leq X \leq 10.0\%$ | $0.0\% \leq X \leq 5.0\%$ | $0.0\% \leq X \leq 3.5\%$ |
| 16:1 ω7c alcohol | $0.0\% \leq X \leq 2.5\%$ | $0.0\% \leq X \leq 2.2\%$ | $0.0\% \leq X \leq 1.9\%$ |
| 16:0 iso | $0.0\% \leq X \leq 5.9\%$ | $4.3\% \leq X \leq 10\%$ | $4.3\% \leq X \leq 5.9\%$ |
| 16:1 ω11c | $8.8\% \leq X$ | $9.0\% \leq X$ | $9.3\% \leq X \leq 16.7\%$ |
| 16:0 | $8.5\% \leq X \leq 20.0\%$ | $5.0\% \leq X \leq 14.4\%$ | $8.5\% \leq X \leq 14.4\%$ |
| 17:0 anteiso | $5.8\% \leq X \leq 10.0\%$ | $3.5\% \leq X \leq 7.9\%$ | $5.8\% \leq X \leq 7.9\%$ |
| 17:0 iso | $0.0\% \leq X \leq 4.3\%$ | $1.7\% \leq X \leq 5.5\%$ | $1.7\% \leq X \leq 4.3\%$ |

Phenotypic characteristics are the most traditional of the methods used to define a species. The "*P. naphthalenovorans*" of the invention has a percentage of phenotypic traits of the isolate PR-N1 in Table 8 that is 80% in a preferred embodiment, 90% in a more preferred embodiment, and 95% in a most preferred embodiment.

Also provided with the current invention is a plurality of isolated bacterial strains that is useful for bioremediation. A combination of *P. validus* strain PR-P1, sphingomonad strain PR-P12, Arthrobacter strain PR-P3, "*P. naphthalenovorans*" strain PR-N5, nocardioform strain PR-N14 is taught in Example 3 as useful for degrading PAHs. In a preferred embodiment, the plurality of bacteria has at least 2 of these strains, in a more preferred embodiment at least 3 of these strains, and in a most preferred embodiment at least 4 of these strains. It is also contemplated that other isolates of these species and genera can be used in the invention. Examples of other suitable strains can be found in Tables 2–4.

Another aspect of the invention is the method to treat PAH-contaminated substrates using the isolated bacterial strains. The method of the invention comprises contacting at least one of the isolated bacterial strains of the invention to the contaminated substrate for a time sufficient to effect removal of the polyaromatic hydrocarbon.

PAH contamination is widespread and prevalent in ecosystems, but more prevalent in ecosystems associated with the marine environment. Sources of PAH contamination include industrial activities and petroleum chemical spills. Substrates suitable for treatment may be solid or liquid. Substrates may be treated in situ or removed from their location and treated elsewhere. Contaminated substrates that may be treated with the bacterial strains of the invention include, but are not limited to, harbor dredge spoils, sediments, wastewater, sea water, soil, sludge and refinery wastes. In a preferred embodiment, the substrate is dredge waste.

When substrates are not suited to the growth of the bacterial strains of the invention, the substrate may be altered in composition. In one embodiment of the method, the solid substrate is mixed with water and optionally aerated. Other contemplated amendments to the substrate include, but are not limited to various co-substrates, alternate carbon sources, emulsifiers and surfactants.

Optionally, plants may be added to the substrate before or after the bacteria is added. This embodiment is particularly advantageous for the bacterial strains that were originally isolated from the rhizosphere. As much of PAH contamination is associated with marine environments, plants that can tolerate saline conditions are particularly appropriate. Plants that are particularly suited to use with the bacterial strains of the invention for bioremediation include, but are not limited to, *Spartina alterniflora, Phragmites australis, Juncus gerardi, Distichlis spicata, Sporobulus aeroides* and other salt marsh grasses.

It is contemplated that the isolated bacterial strains of the invention may be used as alone or in combination with each other. Additionally, the bacterial strains of the invention may be used with other bacterial strains. Other bacterial strains that may be used in conjunction with the stains of the invention include, but are not limited to, other known PAH degraders.

The effective concentration of the bacteria in the method depends on environmental factors, PAH to be degraded, substrate and bacterial strain used. In general, the bacterial strains of the invention should be added so that their concentration on the substrate is $10^4$ to $10^9$ cells/g. Strains may be pre-induced on phenanthrene or another inducer of PAH-degrading enzymes to increase the degradation of high molecular weight PAHs. The concentration of phenanthrene for this induction may be lower than 0.01 ppm, and is likely to vary between bacterial strains. In a preferred embodiment, the concentration of phenanthrene is the lowest concentration that gives adequate induction of the bacterial strain used. The determination of this concentration is without undue experimentation and will be known to those skilled in the art of bacteriology. One experimental protocol that may be used to determine this concentration is found in Example 3.

Additionally provided with the invention is a composition for bioremediation comprising at least one of the bacterial strains of the invention and an environmentally acceptable carrier. An environmentally acceptable carrier may be such compounds as talc, among others. The bacteria may be lyophilized, hydrated or endospores. Also included in the composition may be at least one compound to aid in bioremediation. Additional compounds may enhance bacterial growth on the substrate. Such compounds include, but are not limited to, carbon sources, pH regulators, plant seeds, additional stains of bacteria, surfactants and emulsifiers. Compounds may also be added to increase the amount of PAH degradation. These compounds may affect the bacteria directly, such as with phenanthrene, or may increase the accessability of the PAHs to the bacteria, such as Tween 80. Such compounds include, but are not limited to, phenanthrene, Tween 80 and SDS.

Provided in-accordance with the present invention is a method for isolating new strains of endospore-forming bacteria with PAH-degrading properties. The method to isolate endospore-forming PAH-degrading bacterial strains comprises the steps of enriching heterogenous cultures for bacteria that can grow with PAH as the sole carbon source and screening the strains for endospore formation by killing vegetative bacteria by heat treatment. An example of this method is given in Example 1. The heat treatment can be from 70 to 90° C. for 10 to 20 minutes. Environments that are contaminated with PAHs are particular desirable for obtaining the heterogenous cultures. In a preferred embodiments, the enrichment method of Example 1 is used, and the bacterial population is enriched for isolates that can grow with naphthalene, phenanthrene or bi-phenyl as the sole carbon source. A bacterial culture which is enriched for strains that can grow with each of two or more PAHs as the sole carbon source is particularly preferred.

The aforementioned enrichment method can also be used to isolate species of endospore-forming bacteria with PAH-degrading activities that are effective against other PAHs. By using different PAHs as sole carbon sources in these cultures, bacterial isolates with a variety of PAH-degrading activities can be isolated.

With the features available in the present invention, it is also possible to the directly isolate the bacterial species of the invention using methods well known to those in the art. Standard high stringency hybridization screening of colonies using known genomic sequences of strains PR-N1 (ATCC Accession No. PTA-640), PR-P1 (ATCC Accession No. PTA-643), PR-N4 (ATCC Accession No. PTA-642) and PR-B2 (ATCC Accession No. PTA-641) as probes is also possible, and methods for these screens can be easily performed by one skilled in the art using available protocols. In preferred embodiments, a 16S rRNA gene sequence (SEQ ID NO:1–11) is used as a probe. Hybridization stringencies are use to identify related bacteria that are at least 85% homologous in a preferred embodiment, at least 94% in a more preferred embodiment, and at least 97% in a most preferred embodiment. Any of the morphological, biochemical and physiological traits that are attributed to *P. validus* and "*P. naphthalenovorans*" in the Examples may also be used as the basis of screens that are specific to PAH-degrading Bacillaceae species.

A high stringency hybridization screening can be preformed by methods that will be well known to those of skill in the art, such as methods for identifying bacterial colonies that contain recombinant plasmids (Sambrook et al., *Molecular Cloning*, Cold Spring Harbor Laboratory (1989), Sections 1.85–1.101 (hereinafter "Sambrook et al.")). For example, a high stringency hybridization may be performed, according to the method of Sambrook et al. (1989, supra), using a hybridization solution comprising: 6×SSC, 5× Denhardt's reagent, 0.5% SDS, 100 µg/ml denatured, fragmented salmon sperm DNA. Hybridization is carried out at 65° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes–1 hour at 37° C. in 1×SSC and 1% SDS; (4) 1 hour at 65° C. in 0.1×SSC and 0.5% SDS, changing the solution every 30 minutes.

One common formula for calculating the stringency conditions required to achieve hybridization between nucleic acid molecules of a specified sequence homology (Sambrook et al., 1989, supra):

$$T_m=81.5° C.+16.6\text{Log }[Na+]+0.41(\% G+C)-0.63 (\% \text{ formamide})-600/\#bp \text{ in duplex}$$

As an illustration of the above formula, using [N+]=[0.368] and 50% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C.

The foregoing description set forth the general procedures involved in making and using the present invention. To the extent that specific materials are mentioned, it is merely for purposes of illustration and is not intended to limit the invention. Unless otherwise specified, general cloning procedures, such as those set forth in Sambrook et al., *Molecular Cloning*, Cold Spring Harbor Laboratory (1989) (hereinafter "Sambrook et al.") or Ausubel et al. (eds) *Current Protocols in Molecular Biology*, John Wiley & Sons (1999) (hereinafter "Ausubel et al.") are used.

The following examples are provided to describe the invention in greater detail. They are intended to illustrate, not to limit, the invention.

EXAMPLE I

Isolation and Characterization of Rhizospheric PAH- and PCB-Degrading Bacteria Plant and sediment samples. Salt marsh plant samples were obtained at two sites. The first site, considered to be pristine (uncontaminated) was at the University of Delaware Marine Station at Lewes, Del. A total of six different plant samples were collected at this site in January, 1997 and included *Spartina alterniflora, Spartina patens, Distichlis spicata, Juncus gerardi, Phragmites australis*, and *Sporobolus aeroides*. The second site was Piles Creek, a contaminated tributary of Arthur Kill located in Linden, N.J. Piles Creek was chosen for obtaining marsh plant and sediment samples based on its accessibility and contamination levels. Estuarine sediment and *Spartina alterniflora* plant samples were obtained at low tide from Piles Creek in February and July, 1997. The plant and sediment samples were transported on ice back to the laboratory where they were stored at 4° C. until analyzed and used for experiments.

Bacterial reference strains and media. Cultures of the following isolates were purchased from the American Type Culture Collection (Rockville, Md.) and used as controls and references in the phenotypic and whole-cell fatty acid analyses: *Bacillus brevis* ATCC 8246, *Paenibacillus alvei* ATCC 6344, *Paenibacillus pabuli* ATCC 43 899, *Paenibacillus polymyxa* ATCC 842, and *Paenibacillus validus* ATCC 43897.

Mineral salts basal (MSB) medium (Stanier et al., 1966, J. Gen. Microbiol. 43:159–271) was used for enrichment cultures, isolation and growth substrate tests. Solid minimal medium contained 2% noble agar (Difco Laboratories, Detroit, Mich.). Stock concentrations (100 mg ml$^{-1}$) of naphthalene, biphenyl and phenanthrene were dissolved in dimethyl formamide and added to liquid medium at a final concentration of 1 mg ml$^1$. Naphthalene and biphenyl were added in the vapor phase as crystals in the petri dish lid for solid medium. Phenanthrene was added as a 2% noble agar overlayer onto MSB agar plates at a final concentration of 1 mg ml$^{-1}$.

Bacterial strains were grown on trypticase soy (Beckton Dickinson & Co., Cockeysville, Md.) agar plates for various phenotypic and fatty acid methyl ester analyses. The bacteria were routinely grown aerobically at 30° C. except where indicated. Strains were maintained on minimal medium at 4° C., and long-term storage was in 50% glycerol at −80° C.

Enrichment and isolation of PAH-degrading bacterial strains. Bacterial enrichment cultures were established in 50 ml MSB medium using naphthalene, phenanthrene or biphenyl as the sole source of carbon. Plant rhizosphere and contaminated estuarine sediment were used as inoculum for the enrichment cultures. Rhizosphere samples were obtained by splitting open the plant root mass thereby exposing the inner roots which had not come in contact with sampling or storage devices. The fine interior roots were aseptically cut and collected and 1 gram of root material was added to each enrichment culture. Sediment samples were added directly to each enrichment culture using a 1 gram subsample. A total of two enrichment cultures for each substrate were established on each rhizosphere and sediment sample. One set of enrichment cultures was placed directly in a 28° C. environmental chamber and shaken at 150 rpm. The second set of enrichments was heat treated for 10 min at 80° C. before incubation to enhance isolation of spore-forming gram-positive bacteria. The cultures were monitored for the presence of microorganisms by gram staining and microscopy and subcultured into fresh MSB medium when growth was detected. After 3 to 4 subcultures, the bacteria were plated onto MSB agar plates containing the same substrate as the enrichment.

Phenotypic characterizations. PAH-degrading isolates were morphologically and phenotypically characterized and compared to type strains using; phase-contrast microscopy, whole-cell fatty acid profiles using the Sherlock Microbial Identification System (Newark, DE), API 20E and 50CH system tests (bioM rieux Vitek, Inc., Hazelwood, Mo.), starch and casein hydrolysis, and the effects of temperature, anaerobiosis and salinity on growth. In addition, the ability of several selected strains to grow on various aromatic substrates was also examined. Several of the gram-positive strains were analyzed for their ability to grow on a variety of aromatic compounds including naphthalene, phenanthrene, biphenyl, phthalate, gentisate, o-, m- and p-hydroxybenzoate, and benzoate. Naphthalene, biphenyl and phenanthrene were added to MSB agar plates as described in the section on bacterial reference strains and media. The organic acids were added to media at a final concentration of 5–10 mM and as sodium salts when necessary.

Phase-contrast microscopy was used for the morphological examination of bacterial cells. The strains to be tested were inoculated into 2 ml of trypticase soy broth (TSB) and incubated on a rotary wheel for 24 h at 28° C. The cells were examined for motility and morphology at 24, 48 and 72 h by placing a drop of culture onto 1% agarose-coated and non-coated glass slides. The agarose coating allowed for more detailed examination and photography of motile cells.

Whole-cell fatty acid analyses were performed on all of the isolates by growing the cells for 24 h on trypticase soy agar (TSA). Cellular fatty acids were extracted, methylated, and detected with a Hewlett Packard model 5890 Series II gas chromatograph and were identified using the Sherlock Microbial Identification System (Operating Manual Version 5, MIDI, Inc.) and the Aerobe (TSBA version 3.9) database. In addition, the Microbial Identification System includes cluster analysis and principle component analysis programs for establishment of relationships among strains (i.e. Euclidean distance).

Isolation and identification of PAH-degrading bacterial strains. Bacterial enrichment cultures were established on all of the Delaware plant rhizosphere samples using naphthalene as the sole source of carbon. Table 2 lists the different bacteria isolated from these plants. The low number and diversity of bacteria isolated from this site was expected due to its pristine nature.

TABLE 2

Naphthalene-degrading bacteria isolated by enrichment from the rhizosphere of pristine salt marsh plants obtained at the University of Delaware Marine Station at Lewes, Delaware.

| Strain | Heat Treatment[a] | Plant species[b] | Bacterial Identification[c] | Similarity Index[d] |
|---|---|---|---|---|
| Salt-N1 | No | Spartina alterniflora | Pseudomonas fluorescens | 0.59 |
| Salt-N2 | No | Spartina alterniflora | Pseudomonas putida | 0.81 |
| JG-N1 | Yes | Juncus gerardi | Paenibacillus validus | 0.80 |
| JG-N2 | No | Juncus gerardi | Paenibacillus validus | 0.81 |
| JG-N3 | Yes | Juncus gerardi | Paenibacillus validus | 0.87 |
| DS-N1 | Yes | Distichlis spicata | Bacillus brevis | 0.45 |
| DS-N2 | No | Distichlis spicata | Paenibacillus validus | 0.92 |
| DS-N3 | Yes | Distichlis spicata | Paenibacillus validus | 0.81 |
| SA-N1 | Yes | Sporobolus aeroides | Paenibacillus pabuli | 0.13 |

[a]Sample enrichments heat treated for 10 min. at 80° C. prior to incubation.
[b]No isolates were obtained from rhizosphere samples taken from *Phragmites australis*.
[c]Tentative identification based on fatty acid methyl ester profiles.
[d]Similarity index (SI) refers to the degree of identity to the MIDI library database. An excellent identification corresponds to a SI of ≧0.6, good identification ranges between 0.4–0.6 and a poor identification corresponds to a SI of ≦0.4.

In contrast, a total of 41 strains have been isolated from *Spartina alterniflora* plant and sediment samples obtained from contaminated Piles Creek in New Jersey, using either naphthalene, phenanthrene or biphenyl as the sole source of carbon (Tables 3 and 4). Heat treatment (80° C. for 10 minutes) prior to enrichment was included for each of the substrates tested in an attempt to isolate endospore-forming gram-positive bacteria. Endospore-forming bacteria able to degrade PAHs are considered more favorable for bioremediation purposes due to their ability to survive adverse environmental conditions (i.e., cold, dry). Table 3 and Table 4 list the Piles Creek isolates obtained from the sediment and rhizosphere, respectively, for each of the substrates tested. The heat treatment was successful in isolating gram-positive endospore-forming bacteria.

TABLE 3

Identification of PAH-degrading bacteria isolated by enrichment from contaminated sediment collected at Piles Creek, New Jersey.

| Strain | Heat treatment[a] | Bacterial Identification[b] | Similarity Index[c] |
|---|---|---|---|
| Naphthalene Gram-negative: | | | |
| PS-N2 | No | Pseudomonas fluorescens | 0.47 |
| PS-N4 | No | Pseudomonas stutzeri | 0.89 |
| PS-N5 | No | Pseudomonas stutzeri | 0.86 |
| Gram-positive: | | | |
| PS-N1 | Yes | Paenibacillus pabuli | 0.26 |
| PS-N6 | Yes | Paenibacillus validus | 0.34 |
| PS-N3 | No | Nocardia asteroides | 0.71 |
| Phenanthrene Gram-negative: | | | |
| PS-P2 | No | Alcaligenes xylosoxydans | 0.65 |

TABLE 3-continued

Identification of PAH-degrading bacteria isolated by enrichment from contaminated sediment collected at Piles Creek, New Jersey.

| Strain | Heat treatment[a] | Bacterial Identification[b] | Similarity Index[c] |
|---|---|---|---|
| Gram-positive: | | | |
| PS-P1 | No | Mycobacterium sp. | not applicable |

[a]Sample enrichments heat treated for 10 min. at 80° C. prior to incubation.
[b]Tentative identification based on fatty acid methyl ester profiles.
[c]Similarity index (SI) refers to the degree of identity to the MIDI library database. An excellent identification corresponds to a SI of ≧0.6, good identification ranges between 0.4–0.6 and a poor identification corresponds to a SI of ≦0.4.

TABLE 4

Identification of PAH-degrading bacteria isolated by enrichment from the rhizosphere of Spartina alterniflora growing in contaminated sediment at Piles Creek, New Jersey.

| Strain | Heat treatment[a] | Bacterial Identification[b] | Similarity Index[c] |
|---|---|---|---|
| Naphthalene | | | |
| Gram-negative: | | | |
| PR-N6 | No | Pseudomonas chlororaphis | 0.85 |
| PR-N7 | No | Pseudomonas stutzeri | 0.88 |
| PR-N8 | No | Pseudomonas putida | 0.82 |
| PR-N9 | No | Pseudomonas putida | 0.87 |
| PR-NIO | No | Pseudomonas putida | 0.82 |
| Gram-positive: | | | |
| PR-NL | Yes | Paenibacillus alvei | 0.18 |
| PR-N2 | Yes | Paenibacillus pabuli | 0.06 |
| PR-N3 | Yes | Paenibacillus validus | 0.87 |
| PR-N4 | Yes | Paenibacillus validus | 0.86 |
| PR-N5 | Yes | Paenibacillus pabuli | 0.06 |
| PR-N11 | Yes | Paenibacillus pabuli | 0.06 |
| PR-N12 | Yes | Paenibacillus pabuli | 0.07 |
| PR-N13 | Yes | Paenibacillus validus | 0.81 |
| PR-N16 | Yes | Paenibacillus pabuli | 0.16 |
| PR-N19 | Yes | Paenibacillus validus | 0.93 |
| PR-N20 | Yes | Paenibacillus validus | 0.84 |
| PR-N21 | Yes | Paenibacillus validus | 0.75 |
| PR-N22 | Yes | Paenibacillus validus | 0.81 |
| PR-N14 | No | Nocardia asteroides | 0.77 |
| PR-N15 | No | Nocardia brasiliensis | 0.21 |
| PR-N17 | No | Nocardia asteroides | 0.57 |
| PR-N18 | No | Nocardia asteroides | 0.14 |
| Phenanthrene | | | |
| Gram-negative: | | | |
| PR-P12 | No | Flavobacterium resinovorum | 0.79, |
| Gram-positive: | | | |
| PR-P1 | Yes | Paenibacillus validus | 0.85 |
| PR-P2 | No | Paenibacillus validus | 0.90 |
| PR-P3 | No | Arthrobacter oxydans | 0.46 |
| PR-P6 | Yes | Paenibacillus validus | 0.88 |
| PR-P9 | Yes | Paenibacillus validus | 0.91 |
| PR-PIO | Yes | Paenibacillus validus | 0.91 |
| PR-P11 | Yes | Paenibacillus validus | 0.70 |
| PR-P13 | Yes | Paenibacillus validus | 0.91 |
| Biphenyl | | | |
| Gram-positive: | | | |
| PR-B1 | No | Paenibacillus validus | 0.87 |
| PR-B2 | No | Bacillus brevis | 0.34 |

[a]Sample enrichments heat treated for 10 min. at 80° C. prior to incubation.
[b]Tentative identification based on fatty acid methyl ester profiles.
[c]Similiarity index (SI) refers to the degree of identity to the MIDI library database with ≧0.6 being an excellent match. Good: 0.4–0.6, poor: ≦0.4.

The identification of all strains is based mainly on their fatty acid methyl ester profiles compared to the TBSA MIDI library., An excellent identification corresponds to a similarity index (SI) of >0.6 (1.0 being a perfect match), a good identification corresponds to a SI of 0.4–0.6 and a poor identification corresponds to a SI <0.4. All of the Delaware isolates have a good to excellent identification except for strain SA-N1 isolated from Sporobolus aeroides. This strain has a unique colony morphology (white, highly mucoid) compared to the other gram-positive spore-forming Delaware isolates. Similarly, the gram-positive spore-forming strains exhibiting the lowest similarity index obtained from Piles Creek sediment and rhizosphere samples also share this colony morphology.

A pairwise comparison Euclidean distance dendrogram based on whole-cell fatty acid compositions of the sediment and rhizosphere PAH-degrading isolates was constructed (FIG. 1). The dendrogram provides information about samples that are clustered. For example, samples that are joined at lower levels of the dendrogram are more closely related than those that are joined at higher levels. A Euclidean Distance of 10 or less may be considered to be the same species, 6 or less the same subspecies and 2.5 or less as two different runs of the same strain. The isolates fall within three main groups (FIG. 1). Group I includes the endospore-forming gram-positive bacteria. Group 2 includes the gram-positive Nocardioforms and Group 3 includes the gram-negative Pseudomonads.

Phenotypic characterizations. Among all of the isolates, the gram-positive isolates were able to degrade a wider range of polyaromatic hydrocarbons than the gram-negative Pseudomonad isolates. In particular, while none of the tested isolates could metabolize pyrene well, the gram-positive isolates were more effective in general than the gram-positive species at metabolizing phenanthrene, fluorene and naphthalene. Among the gram-positive isolates, the spore-forming isolate was very effective at metabolizing naphthalene, biphenyl, fluorene and phenanthrene while the nonspore-forming gram-positive isolates where less-effective at metabolizing biphenyl, fluorene and phenanthrene (Table 5).

TABLE 5

Ability of several isolated to utilize a variety of polyaromatic hydrocarbons.

| | % PAH remaining[b] | | | | |
|---|---|---|---|---|---|
| Strain | Naphthalene | Biphenyl | Fluorene | Phenanthrene | Pyrene |
| Pseudomonads | | | | | |
| PR-N7 | 0 | 85 | 100 | 85 | 90 |
| PR-N6 | 0 | 69 | 78 | 71 | 90 |
| PR-N10 | 40 | 90 | 97 | 89 | 100 |
| PS-P2a | 44 | 51 | 79 | 28 | 100 |
| Gram-positive Non-sporeformers | | | | | |
| PR-N15 | 0 | 84 | 80 | 68 | 100 |
| PR-P3 | 0 | 84 | 42 | 1 | 100 |
| Sporeformer | | | | | |
| PR-P1 | 0 | 0 | 29 | 8 | 100 |

[a]Substrate utilization experiments were performed using dense cell suspensions in minimal salts basal medium containing the appropriate PAH at a final concentration of 100 μM. Samples were incubated at 28° C. at 90 RPM, extracted with hexane and analyzed by gas chromatography.
[b]Percent remaining was calculated relative to uninoculated controls after 11 days of incubation.

EXAMPLE 2
Characterization of Spore-Forming Gram-Positive Strains

Due to the novelty of gram-positive endospore-forming bacteria which are able to degrade PAHs, these particular isolates where characterized further. The spore forming gram-positive isolates exhibited two major colony morphologies, mucoid and nonmucoid, when grown on solid media. A mucoid colony morphology is characterized by a slimy or gummy appearance while a nonmucoid colony morphology is characterized by a smooth clear gray appearance. Phase contrast microscopy showed that all the strains were motile and illustrated typical vegetative-spore-forming life cycle.

smooth clear tan to grey mottled appearance and do not exhibit a mucoid quality.

Figure 3:
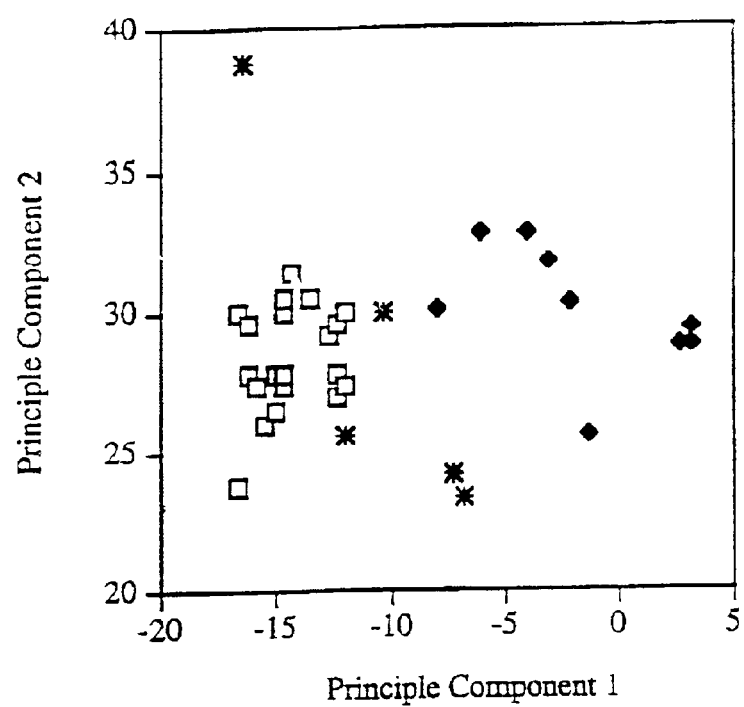
FIG. 3. Two-dimensional plot of the gram-positive endospore-forming PAH-degrading isolates generated by principle-component analysis of whole-cell fatty acid profiles showing distribution into two main groups: Group 1 corresponds to the nonmucoid *Paenibacillus validus* group and Group 2 represents the novel *Paenibacillus* species group exhibiting a mucoid colony morphology.

The gram-positive endospore-forming strains and ATTC type strains were also used for examination using principal component analysis (FIG. 3). The two-dimensional plot shows that all of the PAH-degrading isolates are different from the Paenibacillus and Bacillus type strains tested. One cluster of strains (Paenibacillus validus group) is bordered by Paenibacillus validus and Paenibacillus alvei, but the isolates are clearly distinct from these strains. The second group which includes the unidentified Paenibacillus-like bacteria which exhibit a white-mucoid colony morphology.

TABLE 6

Whole cell fatty acid comparisons of P. validus (ATCC 43897) and the PAH-degrading Paenibacillus isolated as determined by gas chromatograph analysis of their methyl esters.

| Strain | 14:0 1SO | 14:0 | 15:0 iso | 15:0 anteiso | 15:0 | 16:1 ω7c alcohol | 16:0 1SO | 16:1 ω11c | 16:0 | 17:0 anteiso | 17:0 1SO |
|---|---|---|---|---|---|---|---|---|---|---|---|
| Group 1 (Mucoid colony morphology) | | | | | | | | | | | |
| PR-N1 | 0.0 | 2.5 | 5.3 | 51.8 | 0.0 | 0.0 | 5.6 | 9.3 | 14.4 | 7.9 | 3.2 |
| PS-N1 | 2.3 | 2.8 | 6.0 | 55.0 | 1.5 | 0.0 | 5.5 | 9.8 | 9.0 | 6.3 | 1.9 |
| PS-N6 | 1.8 | 2.8 | 5.3 | 52.9 | 1.5 | 1.9 | 5.9 | 12.0 | 8.5 | 5.8 | 1.7 |
| SA-N1 | 1.9 | 2.8 | 5.6 | 49.8 | 2.1 | 1.5 | 5.2 | 12.8 | 8.9 | 6.5 | 2.9 |
| PR-N16 | 1.3 | 2.7 | 6.8 | 45.4 | 3.5 | 1.0 | 4.7 | 11.6 | 12.7 | 6.1 | 4.3 |
| PR-N5 | 0.0 | 3.7 | 4.7 | 47.9 | 0.0 | 0.0 | 4.3 | 16.7 | 13.4 | 6.5 | 2.8 |
| Group 2 (Nonmucoid colony morphology) | | | | | | | | | | | |
| PR-B2 | 3.1 | 1.4 | 15.7 | 48.1 | 0.6 | 2.5 | 9.1 | 3.9 | 4.5 | 4.9 | 5.3 |
| DS-N3 | 2.8 | 1.3 | 14.1 | 48.9 | 0.7 | 3.1 | 7.0 | 5.5 | 4.4 | 5.0 | 4.8 |
| JG-N2 | 3.9 | 1.8 | 14.4 | 49.4 | 0.7 | 3.1 | 8.1 | 5.4 | 4.5 | 3.8 | 3.4 |
| DS-N2 | 3.7 | 1.7 | 13.7 | 50.7 | 0.9 | 2.8 | 7.0 | 5.7 | 4.7 | 4.3 | 3.3 |
| DS-N1 | 2.7 | 1.3 | 14.7 | 50.6 | 0.8 | 2.9 | 6.8 | 5.1 | 4.4 | 4.7 | 4.0 |
| PR-P13 | 2.6 | 2.1 | 13.0 | 49.1 | 0.8 | 2.2 | 6.5 | 7.0 | 6.0 | 4.7 | 4.2 |
| PR-P10 | 2.9 | 1.9 | 12.2 | 49.0 | 0.6 | 3.7 | 6.2 | 7.3 | 5.0 | 4.8 | 3.0 |
| PR-P9 | 2.9 | 1.7 | 12.7 | 46.3 | 1.0 | 3.1 | 7.5 | 7.1 | 5.6 | 5.1 | 4.2 |
| PR-N21 | 3.0 | 1.3 | 13.8 | 53.9 | 0.0 | 2.7 | 7.3 | 4.3 | 4.3 | 4.7 | 3.5 |
| PR-N22 | 3.3 | 1.5 | 13.5 | 53.2 | 0.0 | 2.9 | 7.4 | 4.7 | 4.1 | 4.8 | 3.5 |
| PR-P1 | 3.4 | 1.7 | 11.7 | 54.0 | 0.8 | 3.2 | 6.6 | 6.1 | 4.2 | 4.4 | 3.0 |
| PR-P11 | 3.4 | 3.1 | 8.4 | 51.0 | 1.4 | 2.5 | 5.7 | 8.7 | 7.9 | 4.1 | 1.6 |
| PR-N19 | 2.9 | 1.6 | 11.0 | 50.7 | 1.0 | 2.3 | 8.3 | 5.3 | 6.7 | 5.1 | 3.4 |
| PR-N13 | 2.6 | 1.4 | 10.1 | 52.3 | 1.0 | 1.7 | 7.9 | 4.5 | 7.0 | 5.7 | 4.3 |
| P. validus | 2.7 | 1.8 | 13.2 | 48.0 | 0.9 | 2.2 | 6.8 | 6.9 | 6.4 | 5.3 | 4.3 |

[a]Strains are grown on trypticase soy agar at 28° C. for 24 hours.

Fatty acid methyl ester analysis (FAME, as described in Example 1) determined that the nonmucoid as well as mucoid isolates were members of the genus *Paenibacillus*, formerly part of the genus *Bacillus* (Ash et al., 1993, Antonie van Leeuwenhoek 64:253–260). The predominant fatty acids were 15:0 anteiso (45.4–55.0% of total), 15:0, 16:0 iso, 16:0 and 16:1 ω11c (Table 6). The high percentage of 15:0 anteiso fatty acids is a characteristic of the genus *Paenibacillus*. The mucoid and nonmucoid strains can be distinguished by their 10:0 iso, 16:1 ω11c and 16:0 fatty acid composition (Table 6).

Figure 2:
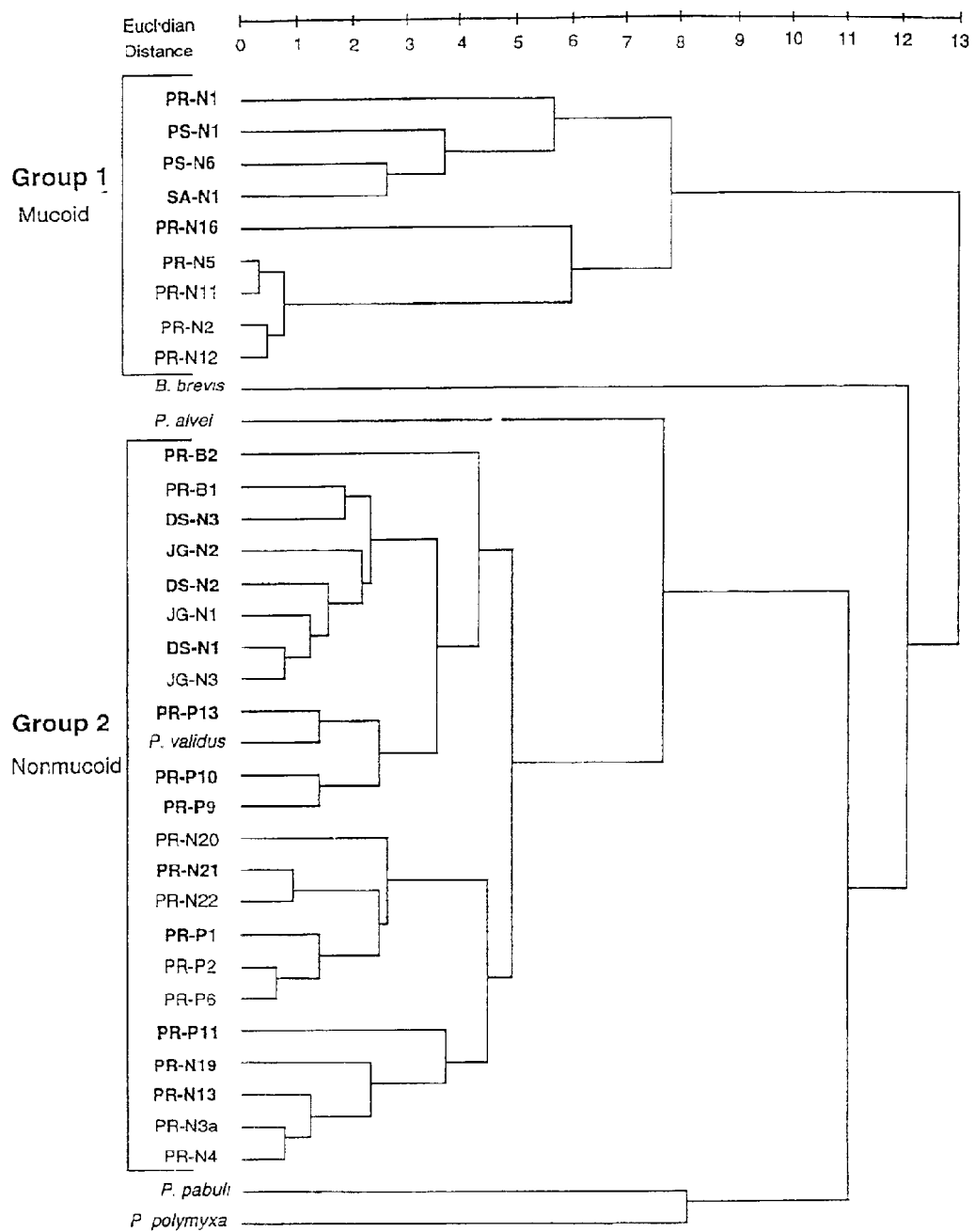
FIG. 2. Euclidean distance dendrogram based on the whole-cell fatty acid compositions of the sediment and rhizosphere PAH-degrading *Paenibacillus* isolates. Piles Creek sediment and *Spartina alterniflora* rhizosphere isolates are denoted as PS and PR, respectively. Isolates obtained from the rhizosphere of *Sporobolus aeroides, Distichlis spicata* or *Juncus gerardi* are denoted as SA, DS or JG, respectively. In addition, strains isolated using naphthalene are indicated by an N, while phenanthrene and biphenyl enriched isolates are denoted by a P and B, respectively. American Type Culture Collection (ATCC) reference strains are in black. The dendrogram program for the Microbial Identification System (MIDI, Inc.) was used to perform a comparative analysis.

A dendrogram was constructed containing only these bacteria and ATCC type strains reveals that the isolates fall within two groups, the non-identified *Paenibacillus*-like bacteria (Group 1) and the *Paenibacillus validus* cluster (Group 2) (FIG. 2). The non-identified group all have low similarity indexes to the MIDI library (Table 7). This group also has a distinct white to grey mucoid colony morphology compared to the *Paenibacillus validus* group which have a

TABLE 7

Comparison of bacterial identification using FAME and partial 16S rRNA gene sequences of the PAH-degrading Paenibacillus strains isolated from the sediment and Rhizosphere of salt marsh plants.

| Strain | Fatty acid methyl ester analysis[a] Identification | Similarity Index | Partial 16S rRNA gene sequence[b] Closest Match | % Homology to P. validus |
|---|---|---|---|---|
| Group 1 (Mucoid colony morphology) | | | | |
| PS-N1 | Paenibacillus alvei | 0.261 | Paenibacillus validus | 93 |
| PR-N1 | Paenibacillus pabuli | 0.181 | Paenibacillus validus | 94 |
| PS-N6 | Paenibacillus validus[c] | 0.334 | Paenibacillus validus | 95 |
| PR-N5 | Paenibacillus pabuli | 0.059 | Paenibacillus validus | 93 |

TABLE 7-continued

Comparison of bacterial identification using FAME and partial 16S rRNA gene sequences of the PAH-degrading Paenibacillus strains isolated from the sediment and Rhizosphere of salt marsh plants.

| Strain | Fatty acid methyl ester analysis[a] | | Partial 16S rRNA gene sequence[b] | |
|---|---|---|---|---|
| | Identification | Similarity Index | Closest Match | % Homology to *P. validus* |
| PR-N16 | *Paenibacillus pabuli* | 0.155 | *Paenibacillus validus* | 93 |
| SA-N1 | *Paenibacillus pabuli* | 0.129 | *Paenibacillus validus* | 93 |
| Group 2 (Nonmucoid colony morphology) | | | | |
| PR-B2 | *Brevibacillus brevis* | 0.340 | *Paenibacillus validus* | 97 |
| DS-N3 | *Paenibacillus validus* | 0.812 | *Paenibacillus validus* | 95 |
| DS-N1 | *Brevibacillus brevis* | 0.454 | *Paenibacillus validus* | 98 |
| PR-P13 | *Paenibacillus validus* | 0.911 | *Paenibacillus validus* | 97 |
| PR-P10 | *Paenibacillus validus* | 0.910 | *Paenibacillus validus* | 96 |
| PR-P9 | *Paenibacillus validus* | 0.909 | *Paenibacillus validus* | 96 |
| PR-N19 | *Paenibacillus validus* | 0.927 | *Paenibacillus validus* | 98 |
| PR-N21 | *Paenibacillus validus* | 0.745 | *Paenibacillus validus* | 95 |
| PR-P1 | *Paenibacillus validus* | 0.849 | *Paenibacillus validus* | 97 |
| PR-P11 | *Paenibacillus validus* | 0.701 | *Paenibacillus validus* | 96 |

[a]FAME identification was performed using the aerobic (TSBA) library version 3.9 of the Microbial Identification System (MIDI, Inc.)
[b]16S rRNA genes were amplified by PCR using universal primers. The PCR products were partially sequenced (~500 bp, ~1.3 kb) and compared to the non-reductant GenBank, EMBL, DDBJ and PDB database (gapped BLAST search) to obtain the most closely matched species.
[c]Listed in the MIDI Library as *Paenibacillus gordonae*, an invalid synonym of *Paenibacillus validus*.

Biochemical characterization using the API 20E and 50CH test systems could distinguish between the two test groups of *Paenibacillus,* the novel mucoid strain and the nonmucoid strains including the *P. validus* ATCC accession strain (Table 8). The mucoid strains were positive while the nonmucoid strains were negative for the Voges-Proskauer test, the production of acetoin, and intermediate in butanediol fermentation. The mucoid strains were all unable to hydrolyze esculin, while the nonmucoid strains in general had this ability. The mucoid strains did not produce acid from glycerol, ribose, D-xylose, ducitol, inositol, amidon and glycogen while the nonmucoid strains in general could produce acid by metabolizing these compounds. Other more general differences between these two groups can be seen Table 8, for example in L-sorbose, cellobiose, D-raffinose, xylitol and β-gentiobiose metabolization.

The group 2, nonmucoid *Paenibacillus* strains were able to utilize a greater number of aromatic substrates that the mucoid *Paenibacillus* (Table 9). The nonmucoid *Paenibacillus* strains, in general, were able to utilize naphthalene, phenanthrene, biphenyl, p-hydroxybenzoate and benzoate, while the mucoid *Paenibacillus* strains could utilize naphthalene, m-hydroxybenzoate, p-hydroxybenzoate and benzoate. The ability of two of the three strains of the mucoid *Paenibacillus* strains to utilize m-hydroxybenzoate and the inability of all three of the mucoid *Paenibacillus* strains to utilize phenanthrene and biphenyl distinguishes them from the nonmucoid *Paenibacillus* strains tested.

TABLE 8

Phenotypic characteristics of PAH degrading strains isolated from sediment and rhizosphere.

| | Group 1 (Mucoid morphology) | | | | | | Group 2 (Nonmucoid morphology) | | | | | | |
|---|---|---|---|---|---|---|---|---|---|---|---|---|---|
| Characteristics | PS-N1 | PR-N1 | PS-N6 | PR-N5 | PR-N16 | SA-N1 | DS-N1 | PR-N20 | PR-N22 | PR-P1 | PR-P13 | PR-P9 | *P. validus* |
| Hydrolysis of: Starch | + | − | − | + | − | + | + | + | + | + | nd[b] | nd | + |
| API 20E Tests[c]: | | | | | | | | | | | | | |
| Citrate | − | − | + | − | + | − | − | − | − | − | − | − | − |
| Urease | + | + | + | + | + | + | + | − | + | + | + | + | + |
| Voges-Proskauer | + | + | + | + | + | + | − | − | − | − | − | − | − |
| Nitrate reduction | − | − | − | + | − | − | − | − | − | − | − | − | − |
| API 50CH Tests[d]: | | | | | | | | | | | | | |
| Esculin hydrolysis | − | − | − | − | − | − | + | − | + | + | + | + | + |
| Acid produced: | | | | | | | | | | | | | |
| Glycerol | − | − | − | − | − | − | + | − | + | + | + | + | + |
| D-Arabinose | − | − | − | − | − | − | − | − | − | + | − | − | − |
| Ribose | − | − | − | − | − | − | + | − | + | + | + | + | + |
| D-Xylose | − | − | − | − | − | − | + | − | + | + | + | + | + |
| D-Fructose | + | + | − | + | + | + | + | − | + | + | + | + | + |
| D-Mannose | + | + | + | + | + | + | + | − | − | + | + | + | + |
| L-Sorbose | + | + | − | + | + | + | − | − | − | − | − | − | − |
| Dulcitol | − | − | − | − | − | − | + | − | + | + | + | + | − |
| Inositol | − | − | − | − | − | − | + | − | + | + | + | + | + |
| Sorbitol | + | − | − | − | − | − | − | − | − | − | − | − | − |

TABLE 8-continued

Phenotypic characteristics of PAH degrading
strains isolated from sediment and rhizosphere.

| | Group 1 (Mucoid morphology) | | | | | | Group 2 (Nonmucoid morphology) | | | | | | |
|---|---|---|---|---|---|---|---|---|---|---|---|---|---|
| Characteristics | PS-N1 | PR-N1 | PS-N6 | PR-N5 | PR-N16 | SA-N1 | DS-N1 | PR-N20 | PR-N22 | PR-P1 | PR-P13 | PR-P9 | P. validus |
| α Methyl-D glucoside | + | + | − | + | + | + | + | − | + | + | + | + | + |
| Cellobiose | − | − | − | − | + | − | + | − | + | − | − | + | + |
| Melibose | − | − | − | + | − | + | + | − | − | + | − | − | + |
| D-Raffinose | − | − | − | − | − | − | + | − | − | + | − | − | + |
| Amidon | − | − | − | − | − | − | + | − | + | + | + | + | + |
| Glycogen | − | − | − | − | − | − | + | + | + | + | + | + | + |
| Xylitol | + | + | − | + | − | + | − | − | − | − | − | − | − |
| β-Gentiobiose | − | − | − | − | − | − | + | − | + | − | − | + | − |
| D-Turanose | + | + | − | + | + | + | + | + | + | + | + | + | + |
| D-Tagatose | − | − | − | − | − | − | − | − | − | + | − | + | − |
| D-Arabitol | − | − | − | − | − | − | − | + | − | − | − | + | − |

[a]All strains are aerobic, motile, catalse positive, negative for casein hydrolysis, growth at 30 and 37° C., no growth at 5 or 55° C., no growth with 3 or 5% NaCl.
[b]nd = not determined.
[c]All isolated negative for: ONPG, gelatin liquefation, arginine dihyrolase, lysine decarboxylase, ornithine decarboxylase, H2S production, indole production and tryptophane deanimase. All strains tested positive for urease.
[d]All isolates produced acid from galactose, D-glucose, mannitol, maltose, saccharose and trehalose.

TABLE 9

Growth of isolates from sediment and rhizosphere on aromatic substrates.

PAH-degrading Paenibacillus species

| | Mucoid colony morphology | | | Non-mucoid colony morphology | | |
|---|---|---|---|---|---|---|
| Substrate | PS-N1 | PR-N1 | PR-N5 | PR-N4 | PR-P1 | PR-B2 |
| Naphthalene | + | + | + | + | + | + |
| Phenanthrene | − | − | − | + | + | − |
| Biphenyl | − | − | − | + | + | + |
| Phthalate | − | − | − | − | − | − |
| Gentisate | − | − | − | − | − | − |
| o-Hydroxy-benzoate | − | − | − | − | − | − |
| m-Hydroxy-benzoate | − | + | + | − | − | nd |
| p-Hydroxy-benzoate | − | + | + | + | + | nd |
| Benzoate | + | + | + | + | + | + |

+, growth of the isolate after 1 week incubation at 30° C.;
no growth; nd, not determined.
Substrate concentrations: Maphthalene and biphenyl were added as crystals in petri-dish lid; phenanthrene (1 mg/ml) was added as an agarose overlayer; organic acids were added to media at 5–10 mM.

The mean base composition of nuclear DNA, as indicated by mol % G+C content, is characteristic of a species. The G+C content of the mucoid and nonmucoid group was 49 and 51 mol %, respectively, but the ranges of the two groups overlapped (Table 10).

Restriction enzyme digestion patterns of genomic DNA from the Paenibacillus strains was performed to determine how many distinct strains were present. EcoR1 digests of the genomic DNA were run on a 0.8% agarose gel and the sizes of the resulting bands compared. These strains are indicated in FIG. 2 in bold type face.

DNA—DNA hybridization experiments can provide semi-quantitative data about the degree of genetic homology between different strains of bacteria. The DNA—DNA hybridization experiment with genomic DNA from the mucoid, nonmucoid and P. validus strains showed only 6% binding of DNA of the mucoid strain, PR-N1, to that of P. validus, while the DNA of PR-N1 showed high percentages of binding to that of the other nonmucoid strains, from 45.5% to 97.0%. Likewise, the degree of binding of P. validus DNA to that of the nonmucoid strains is 72.2% to 79.0%, and 13.2% to that of the mucoid strain PR-N1 (Table 10).

TABLE 10

G + C contents of and DNA binding data
for PAH-degrading Paenibacillus strains.

| | | % DNA binding[a] | |
|---|---|---|---|
| Strain | G + C content[b] (mol %) | PR-N1 | P. validus |
| Group 1 (Mucoid colony morphology) | | | |
| PR-N1 | 46.6 | 100 | 13.2 |
| PS-N1 | 51.5 | 97.0 | |
| PR-N5 | 50.1 | 87.6 | |
| PR-N16 | 49.9 | 87.3 | |
| PS-N6 | 47.7 | 70.9 | |
| SA-N1 | 47.3 | 45.5 | |
| Group 2 (Nonmucoid colony morphology) | | | |
| PR-N19 | 50.1 | | 79.0 |
| PR-P1 | 53.0 | | 72.2 |
| DS-N1 | 48.8 | | |
| PR-P9 | 48.8 | | |
| P. validus ATCC 43897 | 48.7 | 6.0 | 100 |

[a]DNA-DNA hybridization experiments were done by the S1 nuclease method Johnson (1994, In Methods for General and Molecular Bacteriology, pp. 655–682, P. Gernardt, R. G. E. Murry, W. A. Wood and N. K. Kreig (eds.). Washington D.C., American Society of Microbiology).
[b]G + C contents of genomic DNA were estimated by high performance liquid chromatography as described by Mesbah et al. (1989, Int. J. Syst. Bacteriol. 39: 159–167)

Southern hybridizations using the classical genes for naphthalene degradation, pyrene degradation and phenanthrene degradation were performed with genomic DNA from the nonmucoid Paenibacillus strains. Southern hybridizations were performed as recommended by the supplier of the nylon membrane used for hybridization (Biorad). Prehybridization and hybridization were performed at 37° C. Following hybridization, the nylon membrane was washed under low stringency condition (0.1×SSC and 0.1% SDS) at room temperature. EcoR1-digested genomic DNA was probed under low stringency conditions (Goyal and Zyistra 1996, Appl. Environ. Microbiol. 62:230–236) with a 3.5 SalI fragment from *Pseudomonas putida* NCIB-9816-4 (Genbank Accession No. U49496) containing the genes for naphthalene dioxygenase. No genes homologous to the *Pseudomonas putida nah* gene were found indicating the PAH-degrading genes from *Paenibacillus* are novel. Likewise, when genes from pyrene-degrading *Mycobacterium* sp. PY01 (supplied by G. Zylstra) and a phenanthrene-degrading *Comamonas testosteroni* strain (Goyal and Zylstra, J. Ind. Microbiol. Biotechnol. 1997, 19:401–407 and Goyal and Zylestra, 1996, Applied Environ. Microbic. 1996, 62:230–236) were used to probe *Paenibacillus* genomic DNA, no homology was found. It is therefore likely that the nonmucoid strains of *Paenibacillus* isolated have novel genes for naphthalene degradation, pyrene degradation and phenanthrene degradation.

Sequence analyses of 16S rRNA genes were performed on the gram-positive isolates by amplifying the 16S rRNA genes by the polymerase chain reaction (PCR) using the primers 27f and 1522r. The amplified PCR products were purified using the QIA quick PCR purification kit (QIAGEN) according to the manufacturer Ts instructions. DNA sequences were determined directly from the purified PCR products with automated fluorescent Taq cycle sequencing using the API Catalyst 800 and ABI 373A Sequencer (Applied Blosystems, Forester City, Calif.). Approximately 100 ng of the purified DNA is used for one automated fluorescent sequencing reaction. The primers for sequencing were 27f, 704f, 926f, 1242f, 321r, 685r, 907r, 1220r and 1522r (Johnson, 1994, In *Methods for General and Molecular Bacteriology*, pp. 683–700. Gerhardt, Murray, Wood & Krieg, eds. Washington, D.C.: American Society for Microbiology). Partial rRNA sequences for nonmucoid strains DS-N1, PR-B2, PR-N19, PR-P9 and PR-P1 are presented in SEQ ID NOs:1–5, respectively, and mucoid strains SA-N1, PS-N6, PR-N1, PR-N16, PR-N5 and PS-N1 are presented as SEQ ID NOs:6–11.

The 16s rRNA gene sequences were Blast searched for preliminary identification. Detailed gene database searching was performed in the EMBL Data Library. Multiple sequence alignment was done with the PILEUP program in the Genetics Computer Group (GCG) software package using the default parameters. The alignment was edited for the appropriate analysis by using the SUBALIGN and GDE programs from the Ribosomal Database Project (RDP). The phylogenetic analyses were performed with the PHYLIP 3.5 program (Felsenstein, 1989, Cladistics 5:164–166). Kimura's method was used to calculate evolutionary distances (Kimura, 1980, J Mol Evol 16:111–120), from which a phylogenetic dendrogram is drawn by using neighbor-joining analysis (Saitou and Nei, 1987, Mol Biol Evol 4:406–425). The SEQBOOT program was used to obtain confidence levels for neighbor-joining analysis (Felsenstein, 1985, Evolution 39:783–791).

Figure 4:
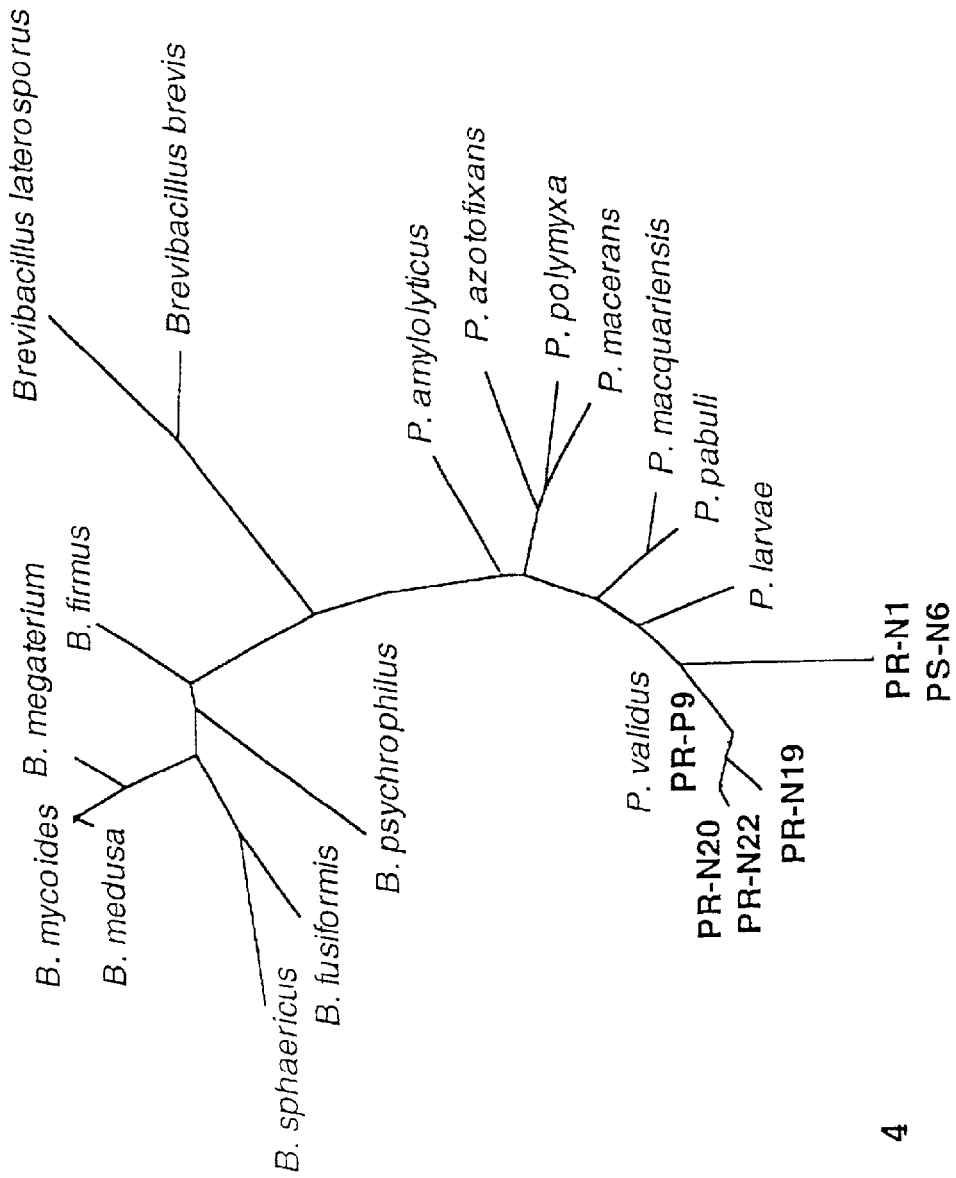
FIG. 4. Neighbor-joining phylogenetic tree of the PAH-degrading isolates and the major groups of the genera *Bacillus, Brevibacillus* and *Paenibacillus*. The tree was constructed using a 368 bp alignment of the 16S rRNA gene. All sequences were aligned to sequences extracted from the Ribosomal Database Project (Michigan State University, East Lansing Mich., Center for Microbial Ecology) using GDE software (Maidak et al., 1999 Nucleic Acids Res. 27:171–173).

16S rRNA gene sequence analysis of isolated from the mucoid group and the nonmucoid group revealed low (~94%) and high (~98%) homology to *P. validus*, respectively (Table 7). In addition, a phylogenetic tree revealed that the nonmucoid group clustered within the species *P. validus* while the mucoid group formed a distinct cluster of *Paenibacillus* (FIG. 4).

The strains can be classified into two species, *Paenibacillus validus* and a new species of *Paenibacillus*.

EXAMPLE III

The use of PAH-Degrading Strains for Bioremediation

The degradation of PAHs, most notably phenanthrene and pyrene, was observed in the sediment slurries with and without *Spartina alterniflora*.

A. Microbial Decontamination of Liquid Culture

Liquid culture decontamination. The ability of *Paenibacillus* strain PR-P1 to degrade PAHs was determined in liquid culture media. Fifty ml serum vials were filled with 10 ml MSB (minimal salts broth) each, final volume. All vials additionally contained 1 ppm of a 4-ring PAH and $10^5$ cells/ml. The 4-ring PAHs used were pyrene, benz[a] anthracene and fluoranthene. Specific treatments additionally comprised 10 ppm phenanthrene or 10 ppm salicylate. Vials with culture were incubated at 28° C. with 200 RPM shaking. Triplicate cultures were sacrificed at days 0, 3, 5 and 7, and analyzed for PAHs.

Extraction and analysis of PAHs. One gram of sample is put into a 7 ml extraction vial. An internal standard (2-methylnaphthalene) is added at a final concentration of 20 ppm and the vial is shaken overnight with 2 ml hexane and 1 ml acetone. The extract is centrifuged at 2,000 RPM for 5 min. and the organic phase removed to a new extraction vial. The remaining material is further extracted with 1 ml hexane for 4 hours, after with it is centrifuges and the organic phases combined. The extract is analyzed for PAH content using a Hewlett Packard 5890 Series II Gas Chromatograph equipped with a HP-5MS column cross-linked with 5% Ph ME siloxane and a 5971 Series mass selective detector.

Figure 5A:
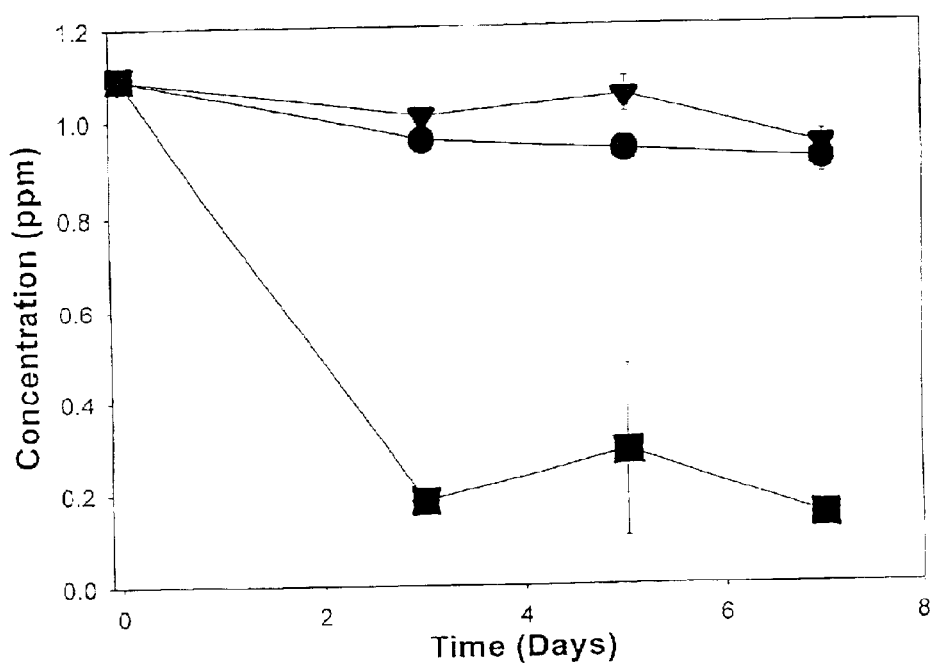
FIG. 5A. Degradation of fluoranthene by Paenibacillus strain PR-P1 over a seven day time course. The three treatments compared include the addition of 10 ppm phenanthrene, strain PR-P1 only and an uninoculated control. Results are the mean of triplicate cultures±standard deviation. Square data points are PR-P1+10 ppm phenanthrene; circular data points are PR-P1 only; and triangular data points are the uninoculated control.
Figure 5B:
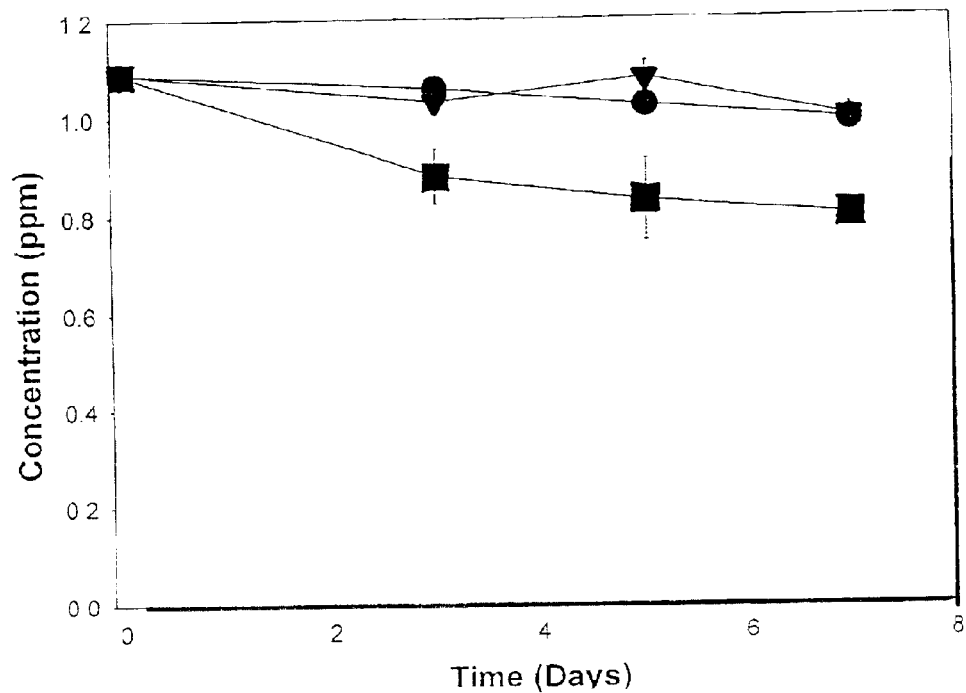
FIG. 5B. Degradation of pyrene by *Paenibacillus* strain PR-P1 over a seven day time course. The three treatments compared include the addition of 10 ppm phenanthrene, strain PR-P1 only and an uninoculated control. Results are the mean of triplicate cultures±standard deviation. Square data points are PR-P1+10 ppm phenanthrene; circular data points are PR-P1 only; and triangular data points are the uninoculated control.

A pure culture of *Paenibacillus validus* strain PR-P1 degraded fluoranthene and pyrene only in the presence of phenanthrene (FIG. 5), indicating that phenanthrene stimulated the co-metabolic utilization of fluoranthene and pyrene. At three days, the treatment containing phenanthrene showed 83% loss of fluoranthene and 20% loss of pyrene. At seven days, 86% loss of fluoranthene and 27% loss of pyrene was observed.

The ability of a consortium of bacteria to degrade PAHs was also determined in liquid culture. The bacterial consortium consisted of *Paenibacillus* strain PR-P1, sphingomonad strain PR-P12, and Arthrobacter strain PR-P3, each inoculated at 108 cells/ml and *Paenibacillus* strain PR-NS and nocardioform strain PR-N14, each inoculated at 104 cells/ml. Treatments of either 10 ppm salicylate or 13 ppm Tween-80 alone with "killed inoculum" and a "no inoculum" control were examined. Culture vials were incubated at 28° C. with 200 RPM shaking. Triplicate cultures were sacrificed, extracted with acetone:hexane (2:1) and analyzed by GC/MS with a 2-methylnaphthalene internal standard.

Figure 6A:
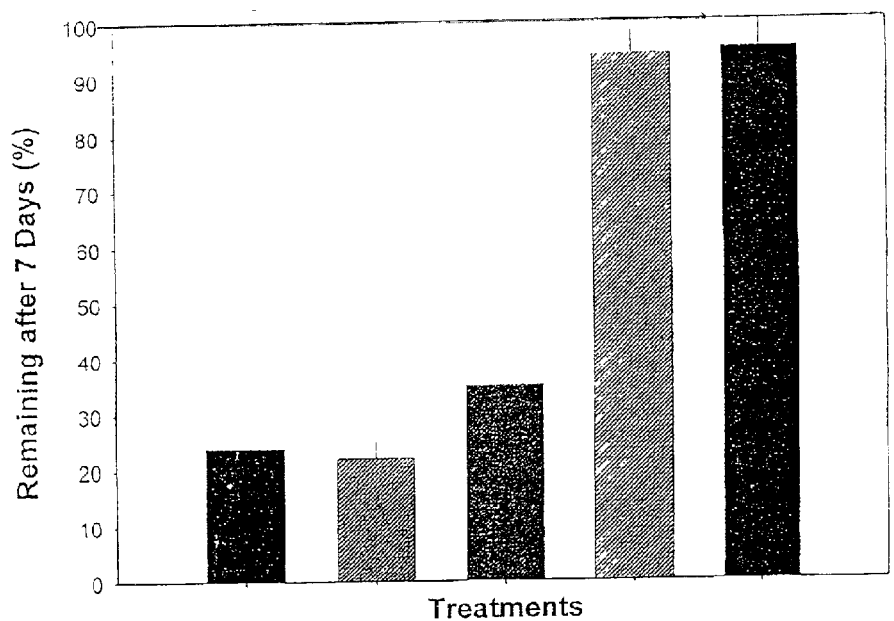
FIG. 6A. Degradation of fluoranthene after seven days incubation in the presence of the bacterial consortium and 10 ppm phenanthrene. Results are the mean of triplicate cultures±standard deviation. From left to right, the bars refer to the treatments consortium+phenanthrene; consortium+phenanthrene+salicylate; consortium+phenanthrene+Tween-80; phenanthrene+Tween-80; and killed consortium+Tween-80.
Figure 6B:
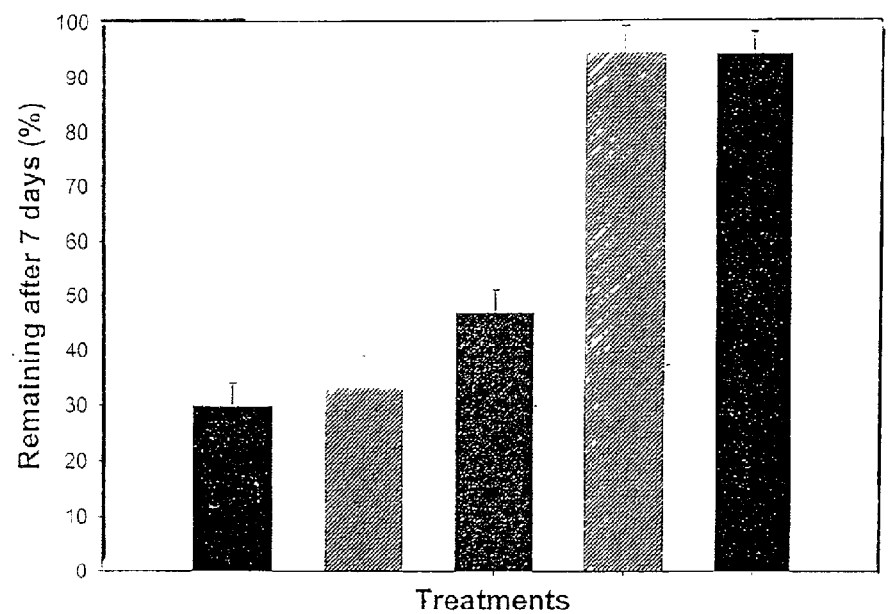
FIG. 6B. Degradation of pyrene after seven days incubation in the presence of the bacterial consortium and 10 ppm phenanthrene. Results are the mean of triplicate cultures±standard deviation. From left to right, the bars refer to the treatments consortium+phenanthrene; consortium+phenanthrene+salicylate; consortium+phenanthrene+Tween-80; phenanthrene+Tween-80; and killed consortium+.Tween-80.
Figure 6C:
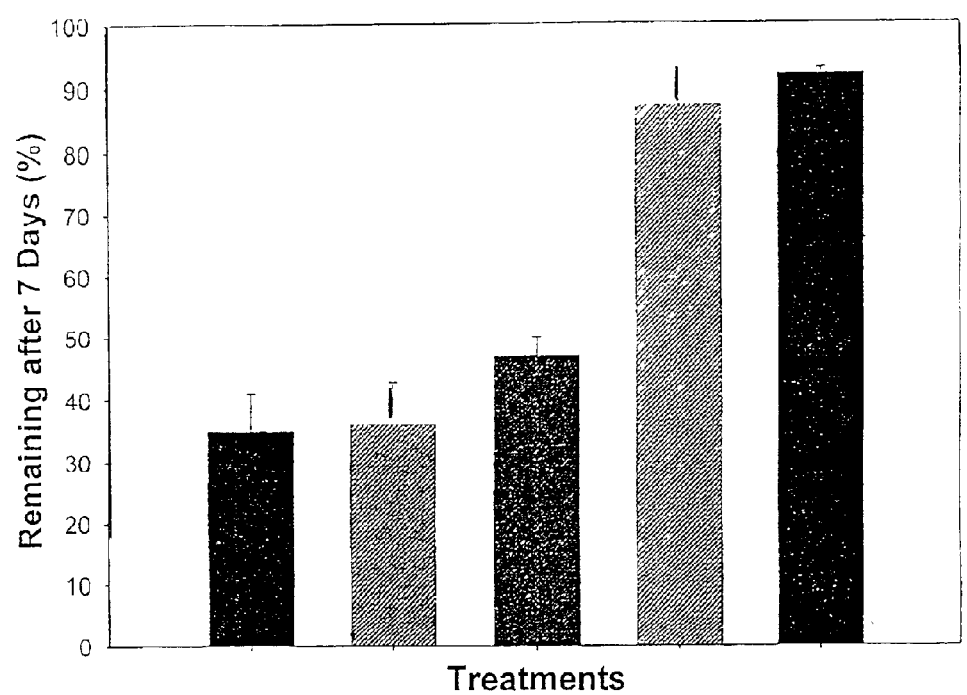
FIG. 6C. Degradation of benz [a]anthracene after seven days incubation in the presence of the bacterial consortium and 10 ppm phenanthrene. Results are the mean of triplicate cultures±standard deviation. From left to right, the bars refer to the treatments consortium+phenanthrene; consortium+phenanthrene+salicylate; consortium+phenanthrene+Tween-80; phenanthrene+Tween-80; and killed consortium+Tween-80.

The consortium of bacteria degraded fluoranthene, pyrene and benz[a]anthracene in the presence of phenanthrene, salicylate and Tween-80 at similar rates (FIG. 6).

B. Plant-Microbial Decontamination of Dredge Material

Plants and plant-associated bacteria were used in the first system to remediate PAH-contaminated dredge material. *Spartina alterniflora* was chosen as the plant species due to its ease of greenhouse propagation and ability to grow in-dredge material. The rhizosphere-associated phenanthrene-degrading strains PR-P1 (*P. validus*) and PR-P3 (Arthrobacter) were chosen as inocula due to their ability to produce spores (PR-P1) and growth on various aromatic substrates (see Table 5). The experiment was performed in triplicate using spiked and non-spiked dredge material for each of the treatments.

Approximately 400 ml of dredge material, obtained from Newtown Creek, was placed into 600 ml glass beakers. Half of the beakers containing dredge material were spiked with a mixture of PAHs dissolved in acetone. The mixture contained a mixture of 2-, 3- and 4-ringed PAHs including naphthalene, biphenyl, fluorene, phenanthrene and pyrene. Spiking the dredge material was required to determine the ability of the strains and plants to fully remediate a highly polluted sediment. Spiked treatments were mixed thoroughly with a concentrated acetone PAH-mixture to give a final concentration of 100 ppm for each compound before the addition of bacteria and plants.

The bacterial strains were grown to mid-to-late log phase in TSB (tryptic soy broth) and harvested by centrifugation at 5,000 rpm for 10 min. The cells were washed and pelleted by centrifugation twice and washed with a mineral salts medium. The washed cells were diluted into 1/10 minimal salts solution and added to the appropriate treatment where they were mixed to a final concentration of approximately $10^7$ cells ml$^{-1}$ for high density inoculation and $10^5$ cells ml$^{-1}$ for low density inoculation. For treatments receiving plants, one S. alterniflora plant (ca. 20–24 in.) was placed in the center of an appropriate beaker by pushing the plant root through the soft dredge material. Each beaker was then flooded with approximately 2 inches of tap water to simulate an estuarine environment and also to stimulate plant growth.

Samples of dredge material for PAH determination and bacterial analyses were obtained at time 0 and at 7 day intervals by plunging a cut 1 cc syringe barrel to the bottom of the beaker and slowly filling the barrel with dredge material as the syringe was pulled out of the beaker. The samples were obtained at random areas within the beakers. For PAH analyses, 2 ml was taken from each treatment and time point and frozen (−20° C.) until extracted. PAH extraction and analysis was performed an aforementioned.

A 1 ml dredge sample was obtained for bacterial analyses for days 0 and 14 only. Bacterial cells were extracted from the dredge material by vortexing with 10 ml of 0.01 M phosphate buffer saline (pH 7.0) containing 0.03% Tween 80 (PBS-T). The bacterial extracts were diluted in PBS-T and plated onto MSB agar plates containing an over-saturated solution of phenanthrene as an agar overlay, and also onto MSB agar plates in which naphthalene was added in the vapor phase as crystals in the petri dish lid. The plates were incubated at 30° C. and examined at 1 and 2 weeks for determination of the number of colony forming units (CFU) per g dredge material.

Analyses of extracts from selected treatments of the small-scale plant-microbial decontamination experiment revealed little to no degradation of the added PAHs. While not the only explanation, the slow rate of degradation may be due to the highly anaerobic nature of the dredge material. The plant-microbial system may therefore be too anaerobic for a feasible and economic time frame for decontamination of dredge material. It is however very likely that this method will be successful if soil is used rather than dredge material. As the bacteria used were isolated from the rhizosphere of *Spartina alterniflora*, their growth is likely to be optimal in this environment. It is significant however that the greenhouse-propagated *Spartina alterniflora* plants were able to live and grow in the contaminated dredge material, and therefore this plant suitable for bioremediation efforts.

C. Microbial Decontamination of Dredge Material Using an Aerobic Slurry System.

A second remediation system for dredge material was devised that used dredge material that had been aerated and mixed with an equal volume of water. This aerobic microbial-slurry model system was designed to determine the rate and extent of microbial degradation of a contaminated dredge-slurry.

For this experiment, approximately equal volumes (500 ml) of dredge material and water were mixed under forced aeration for 1 week prior to bacterial inoculation of slurry microcosms. The microcosms consisted of 50 ml glass serum bottles containing 5 ml of aerated slurry. The degradation experiment was performed in triplicate for each treatment using slurry spiked with PAHs to a final concentration of 50 ppm. The PAHs were added to each individual serum bottle from a concentrated acetone-cocktail as described in the plant-microbe decontamination system. The treatments consisted of sterile and non-sterile slurry, non-sterile slurry+PR-P1 (at $10^9$, $10^7$ and $10^5$ cells ml$^{-1}$) and non-sterile slurry+PR-P3 (at $10^9$, $10^7$ and $10^5$ cells ml$^{-1}$). In addition, 3 treatments using MSB rather than slurry was used to determine the ability of bacterial isolates to degrade a mixture of PAHs in a defined medium versus sediment. These treatments were also spiked with PAHs at a final concentration of 50 ppm and consisted of 5 ml of MSB, MSB+PR-P1 ($10^7$ cells ml$^{-1}$) and MSB+PR-P3 ($10^7$ cells ml$^{-1}$). All the bottles were Teflon-stoppered through which an 18 gauge cotton-plugged needle was pierced. The microcosms were then placed in a 30° C. environmental chamber at 90 rpm.

Sampling for PAH analyses were performed at 8 time points ranging from day 0 to day 49 (7 day sampling interval). The microcosms were frozen at −20° C. until extracted for GC/MS. For PAH analyses, the content of the entire slurry system was extracted overnight with 4 ml hexane and 2 ml acetone by shaking at 200 rpm. The serum bottles were then centrifuged for 5 min at 1,500 rpm and the organic phase was removed to a fresh 7 ml extraction vial. The slurry was further extracted using 2 ml hexane for 4 hours by shaking at 200 rpm. The bottles were centrifuged and the organic phases were combined and analyzed by GC/MS as described above.

Uninoculated and inoculated sediment slurries both showed loss of the 2- and 3-ringed PAH, naphthalene, biphenyl, fluorene and phenanthrene. However, pyrene degradation was only observed in PR-P1 inoculated treatments.

The present invention is not limited to the embodiments described and exemplified above, but is capable of variation and modification without departure from the scope of the appended claims.

What is claimed:

1. An isolated bacterial strain for bioremediation that is *Paenibacillus napthalenovorans* and degrades naphthalene.

2. The isolated bacterial strain of claim 1, which has a whole cell fatty acid composition when grown on trypticase soy agar at 28° C. for 24 hours in which 16:1 ω11c fatty acids comprise at least 8.8%.

3. The isolated bacterial strain of claim 2, in which the whole cell fatty acid composition when grown on trypticase soy agar at 28° C. for 24 hours further comprises at least 5.8% but not more than 10.0% 17:0 anteiso fatty acids.

4. The isolated bacterial strain of claim 1, which has a whole cell fatty acid similarity index, with isolate ATCC Accession No. PTA-640 of greater than 0.4 when both are grown on trypticase soy agar at 28° C. for 24 hours.

5. The isolated bacterial strain of claim 1, which has a 16S rRNA gene sequence that is at least 95% homologous to SEQ ID NO:8.

6. The isolated bacterial strain of claim 1, which has a genomic DNA of which at least 15% binds to genomic DNA of isolate ATCC Accession No. PTA-640.

7. The isolated bacterial strain of claim 1, which is ATCC Accession No. PTA-640.

8. A composition for bioremediation, comprising the bacteria of claim 1 and an ecologically acceptable carrier.

9. A composition for bioremediation, comprising the bacteria of claim 7 and an ecologically acceptable carrier.

* * * * *

SEQUENCE LISTING

<160> NUMBER OF SEQ ID NOS: 11

<210> SEQ ID NO 1
<211> LENGTH: 1130
<212> TYPE: DNA
<213> ORGANISM: Paenibacillus validus
<220> FEATURE:

```
<221> NAME/KEY: misc_feature
<222> LOCATION: (79)..(79)
<223> OTHER INFORMATION: n=a, c, g or t
<220> FEATURE:
<221> NAME/KEY: misc_feature
<222> LOCATION: (81)..(81)
<223> OTHER INFORMATION: n=a, c, g or t
<220> FEATURE:
<221> NAME/KEY: misc_feature
<222> LOCATION: (201)..(201)
<223> OTHER INFORMATION: n=a, c, g or t
<220> FEATURE:
<221> NAME/KEY: misc_feature
<222> LOCATION: (787)..(787)
<223> OTHER INFORMATION: n=a, c, g or t
<220> FEATURE:
<221> NAME/KEY: misc_feature
<222> LOCATION: (1023)..(1023)
<223> OTHER INFORMATION: n=a, c, g or t

<400> SEQUENCE: 1
ttagagtttg atcctggctc aggacgaacg ctggcggcgt gcctaataca tgcaagtcga      60
gcggacttat ccttcgggnt nggttagcgg cggacgggtg agtaacacgt aggcaacctg     120
cctgtaagat cgggataact accggaaacg gtagctaaga ccggatagct ggtttctccg     180
catgggggaa tcatgaaaca ngggcaacc tgtggcttac ggatgggcct gcggcgcatt     240
agctagttgg tggggtaacg gcccaccaag gcgacgatgc gtagccgacc tgagagggtg     300
atcggccaca ctgggactga gacacggccc agactcctac gggaggcagc agtagaggaa     360
tctttccgca atgggcgcaa gcctgacgga gcaacgccgc gtgagtgatg aaggttttcg     420
gatcgtaaag ctctgttgcc aaggaagaac gcctcggaga gtaactgctc tgagggtgac     480
ggtacttgag aagaaagccc cggctaacta cgtgccagca gccgcggtaa tacgtagggg     540
gcaagcgttg tccggaatta ttgggcgtaa agcgcgcgca ggcggtcttt taagtttggt     600
gtttaagccc ggggctcaac cccggttcgc actgaaaact gggagacttg agtgcaggag     660
aggaaagcgg aattccacgt gtagcggtga aatgcgtaga gatgtggagg aacaccagtg     720
gcgaaggcgg ctttctggac tgtaactgac gctgaggcgc gaaagcgtgg ggagcaaaca     780
ggattanata ccctggtagt ccacgccgta acgatgagt gctaggtgtt aggggtttcg     840
atacccttgg tgccgaagta aacacaataa gcactccgcc tggggagtac gctcgcaaga     900
gtgaaactca aaggaattga cggggacccg cacaagcagt ggagtatgtg gtttaattcg     960
aagcaacgcg aagaacctta ccaggtcttg acatccctct gaccggtaca gagatgtacc    1020
ttnccttcgg ggcagaggag acaggtgtg catggttgtc gtcagctcgt gtcgtgagat    1080
gttgggttaa gtcccgcaac gagcgcaacc cttgaactta gttgccagca                1130
```

<210> SEQ ID NO 2
<211> LENGTH: 1641
<212> TYPE: DNA
<213> ORGANISM: Paenibacillus validus
<220> FEATURE:
<221> NAME/KEY: misc_feature
<222> LOCATION: (12)..(12)
<223> OTHER INFORMATION: n=a, c, g or t
<220> FEATURE:
<221> NAME/KEY: misc_feature
<222> LOCATION: (16)..(16)
<223> OTHER INFORMATION: n=a, c, g or t
<220> FEATURE:
<221> NAME/KEY: misc_feature
<222> LOCATION: (18)..(19)
<223> OTHER INFORMATION: n=a, c, g or t
<220> FEATURE:
<221> NAME/KEY: misc_feature

```
<222> LOCATION: (22)..(22)
<223> OTHER INFORMATION: n=a, c, g or t
<220> FEATURE:
<221> NAME/KEY: misc_feature
<222> LOCATION: (28)..(28)
<223> OTHER INFORMATION: n=a, c, g or t
<220> FEATURE:
<221> NAME/KEY: misc_feature
<222> LOCATION: (41)..(41)
<223> OTHER INFORMATION: n=a, c, g or t
<220> FEATURE:
<221> NAME/KEY: misc_feature
<222> LOCATION: (43)..(43)
<223> OTHER INFORMATION: n=a, c, g or t
<220> FEATURE:
<221> NAME/KEY: misc_feature
<222> LOCATION: (48)..(48)
<223> OTHER INFORMATION: n=a, c, g or t
<220> FEATURE:
<221> NAME/KEY: misc_feature
<222> LOCATION: (50)..(50)
<223> OTHER INFORMATION: n=a, c, g or t
<220> FEATURE:
<221> NAME/KEY: misc_feature
<222> LOCATION: (55)..(55)
<223> OTHER INFORMATION: n=a, c, g or t
<220> FEATURE:
<221> NAME/KEY: misc_feature
<222> LOCATION: (57)..(57)
<223> OTHER INFORMATION: n=a, c, g or t
<220> FEATURE:
<221> NAME/KEY: misc_feature
<222> LOCATION: (59)..(59)
<223> OTHER INFORMATION: n=a, c, g or t
<220> FEATURE:
<221> NAME/KEY: misc_feature
<222> LOCATION: (64)..(64)
<223> OTHER INFORMATION: n=a, c, g or t
<220> FEATURE:
<221> NAME/KEY: misc_feature
<222> LOCATION: (68)..(68)
<223> OTHER INFORMATION: n=a, c, g or t
<220> FEATURE:
<221> NAME/KEY: misc_feature
<222> LOCATION: (73)..(73)
<223> OTHER INFORMATION: n=a, c, g or t
<220> FEATURE:
<221> NAME/KEY: misc_feature
<222> LOCATION: (89)..(89)
<223> OTHER INFORMATION: n=a, c, g or t
<220> FEATURE:
<221> NAME/KEY: misc_feature
<222> LOCATION: (92)..(92)
<223> OTHER INFORMATION: n=a, c, g or t
<220> FEATURE:
<221> NAME/KEY: misc_feature
<222> LOCATION: (97)..(97)
<223> OTHER INFORMATION: n=a, c, g or t
<220> FEATURE:
<221> NAME/KEY: misc_feature
<222> LOCATION: (104)..(106)
<223> OTHER INFORMATION: n=a, c, g or t
<220> FEATURE:
<221> NAME/KEY: misc_feature
<222> LOCATION: (109)..(109)
<223> OTHER INFORMATION: n=a, c, g or t
<220> FEATURE:
<221> NAME/KEY: misc_feature
<222> LOCATION: (1116)..(1116)
<223> OTHER INFORMATION: n=a, c, g or t
<220> FEATURE:
<221> NAME/KEY: misc_feature
<222> LOCATION: (1125)..(1125)
<223> OTHER INFORMATION: n=a, c, g or t
<220> FEATURE:
<221> NAME/KEY: misc_feature
<222> LOCATION: (1132)..(1132)
<223> OTHER INFORMATION: n=a, c, g or t
<220> FEATURE:
```

-continued

```
<221> NAME/KEY: misc_feature
<222> LOCATION: (1134)..(1134)
<223> OTHER INFORMATION: n=a, c, g or t
<220> FEATURE:
<221> NAME/KEY: misc_feature
<222> LOCATION: (1145)..(1145)
<223> OTHER INFORMATION: n=a, c, g or t
<220> FEATURE:
<221> NAME/KEY: misc_feature
<222> LOCATION: (1148)..(1149)
<223> OTHER INFORMATION: n=a, c, g or t
<220> FEATURE:
<221> NAME/KEY: misc_feature
<222> LOCATION: (1168)..(1168)
<223> OTHER INFORMATION: n=a, c, g or t
<220> FEATURE:
<221> NAME/KEY: misc_feature
<222> LOCATION: (1174)..(1174)
<223> OTHER INFORMATION: n=a, c, g or t
<220> FEATURE:
<221> NAME/KEY: misc_feature
<222> LOCATION: (1241)..(1241)
<223> OTHER INFORMATION: n=a, c, g or t
<220> FEATURE:
<221> NAME/KEY: misc_feature
<222> LOCATION: (1394)..(1394)
<223> OTHER INFORMATION: n=a, c, g or t
<220> FEATURE:
<221> NAME/KEY: misc_feature
<222> LOCATION: (1406)..(1406)
<223> OTHER INFORMATION: n=a, c, g or t
<220> FEATURE:
<221> NAME/KEY: misc_feature
<222> LOCATION: (1413)..(1413)
<223> OTHER INFORMATION: n=a, c, g or t
<220> FEATURE:
<221> NAME/KEY: misc_feature
<222> LOCATION: (1465)..(1465)
<223> OTHER INFORMATION: n=a, c, g or t
<220> FEATURE:
<221> NAME/KEY: misc_feature
<222> LOCATION: (1490)..(1490)
<223> OTHER INFORMATION: n=a, c, g or t
<220> FEATURE:
<221> NAME/KEY: misc_feature
<222> LOCATION: (1495)..(1495)
<223> OTHER INFORMATION: n=a, c, g or t
<220> FEATURE:
<221> NAME/KEY: misc_feature
<222> LOCATION: (1516)..(1516)
<223> OTHER INFORMATION: n=a, c, g or t
<220> FEATURE:
<221> NAME/KEY: misc_feature
<222> LOCATION: (1531)..(1531)
<223> OTHER INFORMATION: n=a, c, g or t
<220> FEATURE:
<221> NAME/KEY: misc_feature
<222> LOCATION: (1546)..(1546)
<223> OTHER INFORMATION: n=a, c, g or t
<220> FEATURE:
<221> NAME/KEY: misc_feature
<222> LOCATION: (1560)..(1560)
<223> OTHER INFORMATION: n=a, c, g or t
<220> FEATURE:
<221> NAME/KEY: misc_feature
<222> LOCATION: (1569)..(1569)
<223> OTHER INFORMATION: n=a, c, g or t
<220> FEATURE:
<221> NAME/KEY: misc_feature
<222> LOCATION: (1587)..(1587)
<223> OTHER INFORMATION: n=a, c, g or t
<220> FEATURE:
<221> NAME/KEY: misc_feature
<222> LOCATION: (1595)..(1595)
<223> OTHER INFORMATION: n=a, c, g or t
<220> FEATURE:
<221> NAME/KEY: misc_feature
<222> LOCATION: (1599)..(1599)
<223> OTHER INFORMATION: n=a, c, g or t
```

```
<220> FEATURE:
<221> NAME/KEY: misc_feature
<222> LOCATION: (1609)..(1609)
<223> OTHER INFORMATION: n=a, c, g or t
<220> FEATURE:
<221> NAME/KEY: misc_feature
<222> LOCATION: (1611)..(1611)
<223> OTHER INFORMATION: n=a, c, g or t
<220> FEATURE:
<221> NAME/KEY: misc_feature
<222> LOCATION: (1617)..(1620)
<223> OTHER INFORMATION: n=a, c, g or t
<220> FEATURE:
<221> NAME/KEY: misc_feature
<222> LOCATION: (1623)..(1623)
<223> OTHER INFORMATION: n=a, c, g or t
<220> FEATURE:
<221> NAME/KEY: misc_feature
<222> LOCATION: (1630)..(1630)
<223> OTHER INFORMATION: n=a, c, g or t
<220> FEATURE:
<221> NAME/KEY: misc_feature
<222> LOCATION: (1637)..(1638)
<223> OTHER INFORMATION: n=a, c, g or t

<400> SEQUENCE: 2
```

| | | | | | |
|---|---|---|---|---|---|
| ctttgggcaa | angaancnng | tngtgcangg | ttgttgtcag | ntngtgtngn | taaangntng        60 |
| gttnagtncc | gcnacgaggg | caacccttna | anttagntgc | caannnttna | gttgggcact       120 |
| ctaagttgac | tgccggtgac | aaaccggagg | aaggtgggga | tgacgtcaaa | tcatcatgcc       180 |
| ccttatgacc | tgggctacac | acgtactaca | atggccggta | caacgggaag | cgaagtcgcg       240 |
| agatggagcg | aatccttaga | agccggtctc | agttcggatt | gcaggctgca | actcgcctgc       300 |
| atgaagtcgg | aattgctagt | aatcgcggat | cagcatgccg | cggtgaatac | gttcccgggt       360 |
| cttgtacaca | ccgcccgtca | caccacgaga | gtttacaaca | cccgaagtcg | gtggggtaac       420 |
| cgcaaggagc | cagccgccga | aggtgggta | gatgattggg | gtgaagtcgt | aacaaggtag       480 |
| ccgtaatack | gcaaggtscr | gctggactca | cctccttgcg | gccgcccaat | ggttagcggc       540 |
| ggacgggtga | gtaacacgta | ggcaacctgc | ctgtaagatc | gggataacta | ccggaaacgg       600 |
| tagctaagac | cggatagctg | gtttctccgc | atgggggaat | catgaaacat | ggggcaacct       660 |
| atggcttacg | gatgggcctg | cggcgcatta | gctagttggt | ggggtaatgg | cccaccaagg       720 |
| cgacgatgcg | tagccracct | gagagggtga | tcggccacac | tgggactgar | acacggccca       780 |
| ractcctacg | ggaggcagca | gtagggaatc | ttccgcaatg | ggcgcaagcc | tgacggaaca       840 |
| acgccgcgtg | agtgatgaag | gttttcggat | cgtaaagctc | tgttgccaag | gaagaacgcc       900 |
| tcggagagta | actgctctga | gggtgacggt | acttgagaag | aaagccccgg | ctaactacgt       960 |
| gccagcagcc | gcggtaatac | gtaggggca | agcgttgtcc | ggaattattg | ggcgtaaagc      1020 |
| gcgcgcaggc | ggtcttttaa | gtttggtgtt | taagcccggg | gctcaacccc | ggttcgcact      1080 |
| gaaaactggg | agacttgagt | gcaggacagg | aaacangaat | tacanggtgt | ancncagaaa      1140 |
| agtgngannt | gtgtatgaac | accagtgncg | aagncacttg | ctttctgaga | ctgtaactga      1200 |
| cgacattgag | gcgckaaagc | gtggggagca | aacaggatta | natacctgg | tagtccacgc      1260 |
| cgtaaacgat | gagtgctagg | tgttaggggt | ttcgataccc | ttggtgccga | agtaaacaca      1320 |
| ataagcactc | cgcctgggga | gtacgctcgc | aagagtgaaa | ctcaaaggaa | ttgacgggga      1380 |
| cccgcacaag | cagnggagta | tgtggnttaa | ttngaagcaa | cgcgaaaaac | cttaccaggt      1440 |
| cttgacatcc | ctctgaccgg | tacanagatt | gtaccttcc | ttcggggcan | agganacagg      1500 |
| tggtgcatgg | ttgtcntcag | cttgtgtcgt | nagatgttgg | gttaantccg | caaccgagcn      1560 |

-continued

```
caacccttna aacttagttt ccaacanttt atttngccnc tttaacttnc nttgtcnnnn      1620
ccnaaccggn tggaagnngg g                                               1641

<210> SEQ ID NO 3
<211> LENGTH: 1431
<212> TYPE: DNA
<213> ORGANISM: Paenibacillus validus
<220> FEATURE:
<221> NAME/KEY: misc_feature
<222> LOCATION: (66)..(66)
<223> OTHER INFORMATION: n=a, c, g or t
<220> FEATURE:
<221> NAME/KEY: misc_feature
<222> LOCATION: (68)..(69)
<223> OTHER INFORMATION: n=a, c, g or t
<220> FEATURE:
<221> NAME/KEY: misc_feature
<222> LOCATION: (1339)..(1339)
<223> OTHER INFORMATION: n=a, c, g or t
<220> FEATURE:
<221> NAME/KEY: misc_feature
<222> LOCATION: (1344)..(1344)
<223> OTHER INFORMATION: n=a, c, g or t
<220> FEATURE:
<221> NAME/KEY: misc_feature
<222> LOCATION: (1349)..(1349)
<223> OTHER INFORMATION: n=a, c, g or t
<220> FEATURE:
<221> NAME/KEY: misc_feature
<222> LOCATION: (1352)..(1352)
<223> OTHER INFORMATION: n=a, c, g or t
<220> FEATURE:
<221> NAME/KEY: misc_feature
<222> LOCATION: (1370)..(1370)
<223> OTHER INFORMATION: n=a, c, g or t
<220> FEATURE:
<221> NAME/KEY: misc_feature
<222> LOCATION: (1377)..(1377)
<223> OTHER INFORMATION: n=a, c, g or t
<220> FEATURE:
<221> NAME/KEY: misc_feature
<222> LOCATION: (1382)..(1382)
<223> OTHER INFORMATION: n=a, c, g or t
<220> FEATURE:
<221> NAME/KEY: misc_feature
<222> LOCATION: (1386)..(1386)
<223> OTHER INFORMATION: n=a, c, g or t
<220> FEATURE:
<221> NAME/KEY: misc_feature
<222> LOCATION: (1392)..(1392)
<223> OTHER INFORMATION: n=a, c, g or t
<220> FEATURE:
<221> NAME/KEY: misc_feature
<222> LOCATION: (1406)..(1406)
<223> OTHER INFORMATION: n=a, c, g or t
<220> FEATURE:
<221> NAME/KEY: misc_feature
<222> LOCATION: (1408)..(1408)
<223> OTHER INFORMATION: n=a, c, g or t

<400> SEQUENCE: 3
tagagtttga tcctggctca ggacgaacgc tggcggcgtg cctaatacat gcaagtcgag       60
cggacntnnt ccttcgggaa tggttagcgg cggacgggtg agtaacacgt aggcaacctg      120
cctgtaagat cgggataact accggaaacg gtagctaaga ccggatagct ggtttctccg      180
catgggggaa tcatgaaaca cggggcaacc tgtggcttac ggatgggcct gcggcgcatt      240
agctagttgg tggggtaawg gcccaccaag gcgacgatgc gtagccgacc tgagagggtg      300
atcggccaca ctgggactga gacacggccc agactcctac gggaggcagc agtagggaat      360
cttccgcaat gggcgcaagc ctgacggagc aacgccgcgt gagtgatgaa ggttttcgga      420
tcgtaaagct ctgttgccaa ggaagaacgc tcggagagt aactgctctg agggtgacgg      480
```

-continued

```
tacttgagaa gaaagccccg gctaactacg tgccagcagc cgcggtaata cgtaggggc    540 aagcgttgtc cggaattatt gggcgtaaag cgcgcgcagg cggtctttta gtttggtgt    600 ttaagcccgg ggctcaaccc cggttcgcac tgaaaactgg gagacttgag tgcaggagag    660
gaaagcggaa ttccacgtgt agcggtgaaa tgcgtagaga tgtggaggaa caccagtggc    720
gaaggcggct ttctggactg taactgacgc tgaggcgcga aagcgtgggg agcaaacagg    780
attagatacc ctggtagtcc acgccgtaaa cgatgagtgc taggtgttag ggtttcgat    840 acccttggtg ccgaagtaaa cacaataagc actccgcctg ggagtacgc tcgcaacgag    900 tgaaactcaa aggaattgac ggggacccgc acaagcagtg gacgtatgtg gtttaattcg    960
aagcaacgcg aagaacctta ccaggtcttg acatccctct gaccggtaca gagatgtacc   1020
ttcccttcgg ggcagaggag acaggtggtg catggttgtc gtcagctcgt gtcgtgagat   1080
gttgggttaa gtcccgcaac gagcgcaacc cttgaactta gttgccaagg caagaacgcc   1140
tcggagagta actgctctga gggtgacggt acttgagaag aaagcccegg ctaactacgt   1200 gccagcagcc gcggtaatac gtaggggggca agcgttgtcc ggaattattg ggcgtaaagc   1260
gcgcgcaggc ggtctttttaa gtttggtgtt taagcccggg gctcaacccc ggttcgcact   1320
gaaaactggg agacttgant gcangacang antcccgaat tcccctgtn tccggtnaaa   1380 tncctncaca tntggatgac tccccntngc tacggcggcc ttctggaccc t           1431
```

<210> SEQ ID NO 4
<211> LENGTH: 1567
<212> TYPE: DNA
<213> ORGANISM: Paenibacillus validus
<220> FEATURE:
<221> NAME/KEY: misc_feature
<222> LOCATION: (40)..(40)
<223> OTHER INFORMATION: n=a, c, g or t
<220> FEATURE:
<221> NAME/KEY: misc_feature
<222> LOCATION: (70)..(70)
<223> OTHER INFORMATION: n=a, c, g or t

<400> SEQUENCE: 4

```
agtttgatag agtttgatcc tggctcagga cgaacgctgn cggcgtgcct aatacatgca     60
agtcgagcgn acttatcctt cgggataggt tagcggcgga cgggtgagta acacgtaggc    120
aacctgcctg taagatcggg ataactaccg gaaacggtag ctaagaccgg atagctggtt    180
tctccgcatg ggggaatcat gaaacatggg gcaacctgtg gcttacggat gggcctgcgg    240
cgcattagct agttggtggg gtaatggccc accaaggcga cgatgcgtag ccgacctgag    300
agggtgatcg gccacactgg gactgagaca cggcccarac tcctacggga ggcagcagta    360
gggaatcttc cgcaatgggc gcaagcctga cggagcaacg ccgcgtgagt gatgaaggtt    420
ttcggatcgt aaagctctgt tgccaaggaa gaacgcctcg gagagtaact gctctgaggg    480
tgacggtact tgagaagaaa gccccggcta actacgtgcc agcagccgcg gtaatacgta    540
gggggcaagc gttgtccgga attattgggc gtaaagcgcg cgcaggcggt ctttaagtt    600 tggtgtttaa gcccggggct caaccccggt tcgcactgaa aactgggaga cttgagtgca    660
ggagaggaaa gcggaattcc acgtgtagcg gtgaaatgcg tagagatgtg gaggaacacc    720
agtggcgaag gcggctttct ggactgtaac tgacgctgag gcgcgaaagc gtggggagca    780
aacaggatta gatacctggg tagtccacgc cgtaaacgat gagtgctagg tgttaggggt    840
ttcgataccc ttggtgccga agtaaacaca ataagcactc cgcctgggga gtacgctcgc    900
```

-continued

```
aagagtgaaa ctcaaaggaa ttgacgggga cccgcacaag cagtggagta tgtggtttaa    960
ttcgaagcaa cgcgaagaac cttaccaggt cttgacatcc ctctgaccgg tacagagatg   1020
taccttccct tcggggcaga ggagacaggt ggtgcatggt tgtcgtcagc tcgtgtcgtg   1080
agatgttggg ttaagtcccg caacgagcgc aaccctttgaa cttagttgcc agcattttca   1140
gttgggcact ctaagttgac tgccggtgac aaaccggagg aaggtgggga tracgtcaaa   1200
tcatcattgc cccttatgac ctgggctaca cacgtactac aatggccggt acaacgggaa   1260
gcgaagtccg cgagatggag cgaatcctta gaagccggtc tcagttcgga ttgcaggctg   1320
caactcgcct gcatgaagtc ggaattgcta gtaatcgcgg atcagcatgc cgcggtgaat   1380
acgttcccgg gtcttgtaca caccgcccgt cacaccacga gagtttacaa cacccgaagt   1440
cggtggggta accgcaagga gccagccgcc gaaggtgggg tagatgattg gggtgaagtc   1500
gtaacaaggt agccgtatcg gaagggatgc ggctggatca cctccttgcg gccgcccatt   1560
ttttttt                                                             1567
```

```
<210> SEQ ID NO 5
<211> LENGTH: 1400
<212> TYPE: DNA
<213> ORGANISM: Paenibacillus validus
<220> FEATURE:
<221> NAME/KEY: misc_feature
<222> LOCATION: (4)..(4)
<223> OTHER INFORMATION: n=a, c, g or t
<220> FEATURE:
<221> NAME/KEY: misc_feature
<222> LOCATION: (15)..(15)
<223> OTHER INFORMATION: n=a, c, g or t
<220> FEATURE:
<221> NAME/KEY: misc_feature
<222> LOCATION: (19)..(19)
<223> OTHER INFORMATION: n=a, c, g or t
<220> FEATURE:
<221> NAME/KEY: misc_feature
<222> LOCATION: (33)..(33)
<223> OTHER INFORMATION: n=a, c, g or t
<220> FEATURE:
<221> NAME/KEY: misc_feature
<222> LOCATION: (50)..(50)
<223> OTHER INFORMATION: n=a, c, g or t
<220> FEATURE:
<221> NAME/KEY: misc_feature
<222> LOCATION: (68)..(68)
<223> OTHER INFORMATION: n=a, c, g or t
<220> FEATURE:
<221> NAME/KEY: misc_feature
<222> LOCATION: (79)..(79)
<223> OTHER INFORMATION: n=a, c, g or t
<220> FEATURE:
<221> NAME/KEY: misc_feature
<222> LOCATION: (81)..(81)
<223> OTHER INFORMATION: n=a, c, g or t
<220> FEATURE:
<221> NAME/KEY: misc_feature
<222> LOCATION: (1132)..(1132)
<223> OTHER INFORMATION: n=a, c, g or t
<220> FEATURE:
<221> NAME/KEY: misc_feature
<222> LOCATION: (1143)..(1143)
<223> OTHER INFORMATION: n=a, c, g or t
<220> FEATURE:
<221> NAME/KEY: misc_feature
<222> LOCATION: (1156)..(1157)
<223> OTHER INFORMATION: n=a, c, g or t
<220> FEATURE:
<221> NAME/KEY: misc_feature
<222> LOCATION: (1162)..(1162)
<223> OTHER INFORMATION: n=a, c, g or t
<220> FEATURE:
<221> NAME/KEY: misc_feature
```

-continued

```
<222> LOCATION: (1216)..(1217)
<223> OTHER INFORMATION: n=a, c, g or t
<220> FEATURE:
<221> NAME/KEY: misc_feature
<222> LOCATION: (1221)..(1223)
<223> OTHER INFORMATION: n=a, c, g or t
<220> FEATURE:
<221> NAME/KEY: misc_feature
<222> LOCATION: (1232)..(1235)
<223> OTHER INFORMATION: n=a, c, g or t
<220> FEATURE:
<221> NAME/KEY: misc_feature
<222> LOCATION: (1238)..(1238)
<223> OTHER INFORMATION: n=a, c, g or t
<220> FEATURE:
<221> NAME/KEY: misc_feature
<222> LOCATION: (1242)..(1242)
<223> OTHER INFORMATION: n=a, c, g or t
<220> FEATURE:
<221> NAME/KEY: misc_feature
<222> LOCATION: (1246)..(1247)
<223> OTHER INFORMATION: n=a, c, g or t
<220> FEATURE:
<221> NAME/KEY: misc_feature
<222> LOCATION: (1262)..(1262)
<223> OTHER INFORMATION: n=a, c, g or t
<220> FEATURE:
<221> NAME/KEY: misc_feature
<222> LOCATION: (1283)..(1283)
<223> OTHER INFORMATION: n=a, c, g or t
<220> FEATURE:
<221> NAME/KEY: misc_feature
<222> LOCATION: (1306)..(1306)
<223> OTHER INFORMATION: n=a, c, g or t
<220> FEATURE:
<221> NAME/KEY: misc_feature
<222> LOCATION: (1308)..(1309)
<223> OTHER INFORMATION: n=a, c, g or t
<220> FEATURE:
<221> NAME/KEY: misc_feature
<222> LOCATION: (1313)..(1315)
<223> OTHER INFORMATION: n=a, c, g or t
<220> FEATURE:
<221> NAME/KEY: misc_feature
<222> LOCATION: (1319)..(1319)
<223> OTHER INFORMATION: n=a, c, g or t
<220> FEATURE:
<221> NAME/KEY: misc_feature
<222> LOCATION: (1325)..(1326)
<223> OTHER INFORMATION: n=a, c, g or t
<220> FEATURE:
<221> NAME/KEY: misc_feature
<222> LOCATION: (1337)..(1337)
<223> OTHER INFORMATION: n=a, c, g or t
<220> FEATURE:
<221> NAME/KEY: misc_feature
<222> LOCATION: (1342)..(1342)
<223> OTHER INFORMATION: n=a, c, g or t
<220> FEATURE:
<221> NAME/KEY: misc_feature
<222> LOCATION: (1344)..(1344)
<223> OTHER INFORMATION: n=a, c, g or t
<220> FEATURE:
<221> NAME/KEY: misc_feature
<222> LOCATION: (1357)..(1357)
<223> OTHER INFORMATION: n=a, c, g or t
<220> FEATURE:
<221> NAME/KEY: misc_feature
<222> LOCATION: (1361)..(1361)
<223> OTHER INFORMATION: n=a, c, g or t
<220> FEATURE:
<221> NAME/KEY: misc_feature
<222> LOCATION: (1371)..(1371)
<223> OTHER INFORMATION: n=a, c, g or t
<220> FEATURE:
<221> NAME/KEY: misc_feature
<222> LOCATION: (1374)..(1375)
<223> OTHER INFORMATION: n=a, c, g or t
```

<400> SEQUENCE: 5

```
tctngagttt gatcntggnt caggacgaac gcnggcggag tgcctaatan atgcaagttg       60
agcggacnta tccttcganc ncaggttagc ggcggacggg tgagtaamam gtaggcaacc      120
tgcctgtaag atcgggataa ytaccggaaa cggtagctaa gaccggatag ctggtttctc      180
cgcatggggg aatcatgaaa catgggcaa cctgtggctt acggatgggc ctgcggcgca       240
ttagctagtt ggtggggtaa tggcccacca aggcgacgat gcgtagccga cctgagaggk      300
tgatcggcca acactgggac tgagacacgg cccagaytcy tacgggaggc agcagtaggg      360
aatcttccgc aatgggcgca agcctgacgg agcaacgccg cgtgagtgat gaaggttttc      420
ggatcgtaaa gctctgttgc caaggaagaa cgcctcggag agtaactgct ctgagggtga      480
cggtacttga gaagaaagcc ccggctaact acgtgccagc agccgcggta atacgtaggg      540
ggcaagcgtt gtccggaatt attgggcgta agcgcgcgc aggcggtctt ttaagtttgg       600
tgtttaagcc cggggctcaa ccccggttcg cactgaaaac tggagactt gagtgcagga      660 gaggaaagcg gaattccacg tgtagcggtg aaatgcgtag agatgtggag gaacaccagt     720
ggcgaaggcg gctttctgga ctgtaactga cgctgaggcg cgaaagcgtg gggagcaaac      780
aggattagat accctggtag tccacgccgt aaacgatgag tgctaggtgt tagggttttc      840 gataccctttg gtgccgaagt aaacacaata agcactccgc ctggggagta cgctcgcaag   900
agtgaaactc aaaggaattg acggggaccc gcacaagcag tggagtatgt ggtttaattc     960
gaagcaacgc gaagaacctt accaggtctt gacatccctc tgaccggtac agagatgtac   1020
cttcccttcg gggcagagga gacaggtggt gcatggttgt cgtcagctcg tgtcgtgaga    1080
tgttgggtta agtcccgcaa cgagcgcaac ccttgaactt agttgccagc antcaattgg     1140 ggncccccyaa ttkaanngcc gntaacaacc cgaagaaagg tgggaataac ttcaatcctc   1200 ctkccccccta ttaacnnggg nnncccccctt cnnnnatngg cnggtnnacc ggaaaccaaa   1260
tncccaaaat gaaccaatcc ctnaaaaccc ggccccattc cgaatngnna ggnnncacnc    1320 ccccnncctta aattcgnatt gncnattatc cccgaancac nttcccccgg naannacttc    1380
cccggttctg tttaaaaccc                                                 1400
```

<210> SEQ ID NO 6
<211> LENGTH: 757
<212> TYPE: DNA
<213> ORGANISM: Paenibacillus, new species
<220> FEATURE:
<221> NAME/KEY: misc_feature
<222> LOCATION: (217)..(217)
<223> OTHER INFORMATION: n=a, c, g or t
<220> FEATURE:
<221> NAME/KEY: misc_feature
<222> LOCATION: (623)..(623)
<223> OTHER INFORMATION: n=a, c, g or t
<220> FEATURE:
<221> NAME/KEY: misc_feature
<222> LOCATION: (642)..(642)
<223> OTHER INFORMATION: n=a, c, g or t
<220> FEATURE:
<221> NAME/KEY: misc_feature
<222> LOCATION: (712)..(712)
<223> OTHER INFORMATION: n=a, c, g or t
<220> FEATURE:
<221> NAME/KEY: misc_feature
<222> LOCATION: (742)..(742)
<223> OTHER INFORMATION: n=a, c, g or t
<220> FEATURE:
<221> NAME/KEY: misc_feature
<222> LOCATION: (751)..(751)
<223> OTHER INFORMATION: n=a, c, g or t

<400> SEQUENCE: 6

```
cccctggag cggcggacgg gtgagtaaca cgtaggcaac ctgcctgtaa gaccgggata    60
actaccggaa acgtgtagcta agaccggata ggtgattttt ccgcatggag ggatcaagaa   120
acacggtgca agctgtggct tacagatggg cytgcggcgc attagmtagt tggtggggta   180
acggctcacc aaggcgacga tgcgtagccg acctganagg gtgatcggcc acactgggac   240
tgagacacgg cccagactcc tacgggaggc agcagtaggg aatcttccgc aatggacgca   300
agtctgacgg agcaacgccg cgtgagtgaa gaaggttttc ggatcgtaaa gctctgttgc   360
caaggaagaa cgccttgggg agtcactgcc ctgagggtga cggtacttga agaaaagcc    420
ccggctaact acgtgccagc agccgcggta atacgtaggg gcaagcgtt gtccggaatt    480
attgggcgta aagcgcgcgc aggcggccgc ttaagtttgg tgtttaagcc cggggctcaa   540
ccccggatcg caccgaaaac tgggtggctt gagtgcagga gaggaargcg kaaaagttcc   600
acgtgtagcg gtgaaatgcg tanagatgtg gaggaacacc antggcgaaa ggcggctttc   660
tggactgtaa ctgacgctga ggcgcgaaag cgtgggagc aaacaggatt anataccctg   720
gtagtccacg ccgtaaacga tnaattgcta ngtgtta                            757
```

<210> SEQ ID NO 7
<211> LENGTH: 639
<212> TYPE: DNA
<213> ORGANISM: Paenibacillus, new species
<220> FEATURE:
<221> NAME/KEY: misc_feature
<222> LOCATION: (505)..(505)
<223> OTHER INFORMATION: n=a, c, g or t
<220> FEATURE:
<221> NAME/KEY: misc_feature
<222> LOCATION: (524)..(524)
<223> OTHER INFORMATION: n=a, c, g or t
<220> FEATURE:
<221> NAME/KEY: misc_feature
<222> LOCATION: (593)..(593)
<223> OTHER INFORMATION: n=a, c, g or t
<220> FEATURE:
<221> NAME/KEY: misc_feature
<222> LOCATION: (605)..(605)
<223> OTHER INFORMATION: n=a, c, g or t
<220> FEATURE:
<221> NAME/KEY: misc_feature
<222> LOCATION: (631)..(631)
<223> OTHER INFORMATION: n=a, c, g or t

<400> SEQUENCE: 7

```
aagaaacacg gtgcaagctg tggcttacag atgggcctgc ggcgcattag ctagttggtg    60
ggtaacggc tcaccaaggc gacgatgcgt agccgacctg agagggtgat cggccacact   120
gggactgaga cacggcccag actcctacgg gaggcagcag tagggaatct tccgcaatgg   180
acgcaagtct gacggagcaa cgccgcgtga gtgaagaagg ttttcggatc gtaaagctct   240
gttgccaagg aagaacgcct tgggagtca ctgccctgag ggtgacggta cttgagaaga    300
aagcccggc taactacgtg ccagcagccg cggtaatacg taggggcaa gcgttgtccg    360
gaattattgg gcgtaaagcg cgcgcaggcg gccgcttaag tttggtgtat aagcccgggg   420
ctcaaccccg gatcgcaccg aaaactgggt ggcttgagtg caggagagga aagcggaatt   480
ccacgtgtag cggtgaaatg cgtanagatg tggaggaaca ccantggcga aggcggcttt   540
ctggactgta actgacgctg aggcgcgaaa gcgtggggag caaacaggat tanataccct   600
ggtantccac gccgtaaacg atgaatgcta ngtgttagg                          639
```

<210> SEQ ID NO 8
<211> LENGTH: 1551
<212> TYPE: DNA
<213> ORGANISM: Paenibacillus, new species

<400> SEQUENCE: 8

| | | | | | |
|---|---|---|---|---|---|
| cctagagttt | gatcctggct | caggacgaac | cgctggcggc | gtgcctaata | catgcaagtc | 60 |
| gagcgctagg | ggtgctccct | tagggagac | ctcctggagc | ggcggacggg | tgagtaacac | 120 |
| gtaggcaacc | tgcctgtaag | accgggataa | ctaccggaaa | cggtagctaa | gaccggatag | 180 |
| gtggtttctc | cgcatggagg | gatcaagaaa | cacggtgcaa | gctgtggctt | acagatgggc | 240 |
| ctgcggcgca | ttagctagtt | ggtggggtaa | cggctcacca | aggcgacgat | gcgtagccga | 300 |
| cctgagaggg | tgatcggcca | cactgggact | gagacacggc | ccagactcct | acgggaggca | 360 |
| gcagtaggga | atcttccgca | atggacgcaa | gtctgacgga | gcaacgccgc | gtgagtgaag | 420 |
| aaggttttcg | gatcgtaaag | ctctgttgcc | aaggaagaac | gccttgggga | gtcactgccc | 480 |
| tgagggtgac | ggtacttgag | aagaaagccc | cggctaacta | cgtgccagca | gccgcggtaa | 540 |
| tacgtagggg | gcaagcgttg | tccggaatta | ttgggcgtaa | agcgcgcgca | ggcggccgct | 600 |
| taagtttggt | gtataagccc | ggggctcaac | cccggatcgc | accgaaaact | gggtggcttg | 660 |
| agtgcaggag | aggaaagcgg | aattccacgt | gtagcggtga | aatgcgtaga | gatgtggagg | 720 |
| aacaccagtg | gcgaaggcgg | ctttctggac | tgtaactgac | gctgaggcgc | gaaagcgtgg | 780 |
| ggagcaaaca | ggattagata | ccctggtagt | ccacgccgta | aacgatgagt | gctaggtgtt | 840 |
| aggggtttcg | atacccttgg | tgccgaagtc | aacacaataa | gcactccgcc | tggggagtac | 900 |
| gctcgcaaga | gtgaaactca | aaggaattga | cggggacccg | cacaagcagt | ggagtatgtg | 960 |
| gtttaattcg | aagcaacgcg | aagaaccta | ccaggtcttg | acatcccttt | gaccggtaca | 1020 |
| gagatgtacc | tttccttcgg | gacagaggag | acaggtggtg | catggttgtc | gtcagctcgt | 1080 |
| gtcgtgagat | gttgggttaa | gtcccgcaac | gagcgcaacc | cttgagctta | gttgccagca | 1140 |
| ttaagttggg | cactctaagt | tgactgccgg | tgacaaaccg | gaggaaggtg | gggatgacgt | 1200 |
| caaatcatca | tgccccttat | gacctgggct | acacacgtac | tacaatggcc | ggtacaacgg | 1260 |
| gaagcgaagg | agcgatccgg | agcgaatcct | tataagccgg | tctcagttcg | gattgcaggc | 1320 |
| tgcaactcgc | ctgcatgaag | tcggaattgc | tagtaatcgc | ggatcagcat | gccgcggtga | 1380 |
| atacgttccc | gggtcttgta | cacaccgccc | gtcacaccac | gagagtttac | aacacccgaa | 1440 |
| gtcggtgggg | taaccgcaag | gagccagccg | ccgaaggtgg | ggtagatgat | tggggtgaag | 1500 |
| tcgtaagcaa | ggtagccgta | tcggaaggtg | cggctggatc | acctccttaa | a | 1551 |

<210> SEQ ID NO 9
<211> LENGTH: 1476
<212> TYPE: DNA
<213> ORGANISM: Paenibacillus, new species
<220> FEATURE:
<221> NAME/KEY: misc_feature
<222> LOCATION: (256)..(256)
<223> OTHER INFORMATION: n=a, c, g or t
<220> FEATURE:
<221> NAME/KEY: misc_feature
<222> LOCATION: (276)..(276)
<223> OTHER INFORMATION: n=a, c, g or t

<400> SEQUENCE: 9

| | | | | | |
|---|---|---|---|---|---|
| tcccttaggg | gagacctcct | ggagcggcgg | acgggtgagt | aacacgtagg | caacctgcct | 60 |
| gtaagaccgg | gataactacc | ggaaacggta | gctaagaccg | gataggtgat | ttctccgcat | 120 |

US 6,905,864 B2

```
ggagggatca agaaacacgg tgcaagctgt ggyttacaga tgggcctgcg gcgcattagc        180
tagttggtgg ggtaacggct maccaagttg cgacgatgcg tagccgacct gagagggtga        240
tcggccacac tgggantgag acacggccca gactcntacg ggaggcagca gtagggaatc        300
ttccgcaatg gacgcaagtc tgacggagca acgccgcgtg agtgaagaag gttttcggat        360
cgtaaagctc tgttgccaag gaagaacgcc ttggggagtc actgccctga gggtgacggt        420
acttgagaag aaagccccgg ctaactacgt gccagcagcc gcggtaatac gtaggggca         480 agcgttgtcc ggaattattg ggcgtaaagc gcgcgcaggc ggccgcttaa gtttggtgta        540
taagcccggg gctcaacccc ggatcgcacc gaaaactggg tggcttgagt gcaggagagg        600
aaagcggaat tccacgtgta kcggtgaaat gcgtagagat gtggaggaac accagtggcg        660
aaggcggctt tctggactgt aactgacgct gaggcgcgaa agcgtgggga gcaaacagga        720
ttagataccc tggtagtcca cgccgtaaac gatgagtgct aggtgttagg gtttcgata         780 cccttggtgc cgaagtcaac acaataagca ctccgcctgg ggagtacgct cgcaagagtg        840
aaacttaaag gaattgacgg ggacccgcac aagcagtgga gtatgtggtt taattcgaag        900
caacgcgaag aaccttacca ggtcttgaca tcccttttgac cggtacagag atgtacctt      960 ccttcgggac agaggagaca ggtggtgcat ggttgtcgtc agctcgtgtc gtgagatgtt       1020
gggttaagtc ccgcaacgag cgcaaccctt gagcttagtt gccagcatta agttgggcac       1080
tctaagttga ctgccggtga caaaccggaga gaaggtgggg atgacgtcaa atcatcatgc      1140
cccttatgac ctgggctaca cacgtactac aatggccggt acaacgggaa gcgaaggagc       1200
gatccggagc gaatccttat aagccggtct cagttcggat tgcaggctgc aactcgcctg       1260
catgaagtcg gaattgctag taatcgcgga tcagcatgcc gcggtgaata cgttcccggg       1320
tcttgtacac accgcccgtc acaccacgag agtttacaac cccgaagtc ggtggggtaa        1380 ccgcaaggag ccagccgccg aaggtggggt agatgattgg ggtgaagtcg taacaaggta       1440
gccgtatcgg aagtgcggc tggatcacct ccttaa                                  1476
```

```
<210> SEQ ID NO 10
<211> LENGTH: 1545
<212> TYPE: DNA
<213> ORGANISM: Paenibacillus, new species
<220> FEATURE:
<221> NAME/KEY: misc_feature
<222> LOCATION: (2)..(2)
<223> OTHER INFORMATION: n=a, c, g or t
<220> FEATURE:
<221> NAME/KEY: misc_feature
<222> LOCATION: (4)..(4)
<223> OTHER INFORMATION: n=a, c, g or t
<220> FEATURE:
<221> NAME/KEY: misc_feature
<222> LOCATION: (12)..(12)
<223> OTHER INFORMATION: n=a, c, g or t
<220> FEATURE:
<221> NAME/KEY: misc_feature
<222> LOCATION: (30)..(30)
<223> OTHER INFORMATION: n=a, c, g or t
<220> FEATURE:
<221> NAME/KEY: misc_feature
<222> LOCATION: (34)..(34)
<223> OTHER INFORMATION: n=a, c, g or t

<400> SEQUENCE: 10
tngngtttga tnctgggtta ggacggaagn tggnggggtg cctaatacat gcaagtcgag        60
cgctaggggt gctcccttag gggagccccc ctggagcggc ggacgggtga gtaacacgta       120
```

```
ggcaacctgc ctgtaagacc gggataacta ccggaaacgg tagctaagac cggataggtg      180 attttttccgc atggagggat caagaaacac ggtgcaagct gtggcttaca gatgggcctg     240
cggcgcatta gctagttggt ggggtaacgg ctcaccaagg cgacgatgcg tagccgacct     300
gagaggtgat cggccacact gggatgagac acggcccaga ctctacggga ggcagcagta    360
gggaatcttc cgcaatggac gcaagtctga cggagcaacg ccgcgtgagt gaagaaggtt    420
ttcggatcgt aaagctctgt tgccaaggaa gaacgccttg gggagtcact gccctgaggg    480
tgacggtact tgagaagaaa gccccggcta actacgtgcc agcagccgcg gtaatacgta    540
gggggcaagc gttgtccgga attattgggc gtaaagcgcg cgcaggcggc cgcttaagtt    600
tggtgtataa gcccggggct caaccccgga tcgcaccgaa aactgggtgg cttgagtgca    660
ggagaggaaa gcgggaattc cacgtgtagc ggtgaaatgc gtagagatgt ggaggaacac    720
cagtggcgaa ggcggctttc tggactgtaa ctgacgctga ggcgcgaaag cgtggggagc    780
aaacaggatt agataccctg gtagtccacg ccgtaaacga tgagtgctag gtgttagggg    840
tttcgatacc cttggtgccg aagtcaacac aataagcact ccgcctgggg agtacgctcg    900
caagagtgaa actcaaagga attgacgggg acccgcacaa gcagtggagt atgtggttta    960
attcgaagca acgcgaagaa ccttaccagg tcttgacatc cctctgaccg gtacagagat    1020
gtacctttcc ttcgggacag aggagacagg tggtgcatgg ttgtcgtcag ctcgtgtcgt    1080
gagatgttgg gttaagtccc gcaacgagcg caaccccttga gcttagttgc cagcattaag    1140
ttgggcactc taagttgact gccggtgaca accggaggaa ggtggggat gacgtcaaat    1200 catcatgccc cttatgacct gggctacaca cgtactacaa tggccggtac aacgggaagc    1260
gaaggagcga tccggagcaa atccttataa gccggtctca gttcggattg caggctgcaa    1320
ctcgcctgca tgaagtcgga attgctagta atcgcggatc agcatgccgc ggtgaatacg    1380
ttcccgggtc ttgtacacac cgcccgtcac accacgagag tttacaacac ccgaagtcgg    1440
tggggtaacc gcaaggagcc agccgccgaa ggtggggtag atgattgggg tgaagtcgta    1500
acaaggtagc cgtatcggaa ggtgcggctg gatcacctcc ttaaa                     1545
```

<210> SEQ ID NO 11
<211> LENGTH: 1554
<212> TYPE: DNA
<213> ORGANISM: Paenibacillus, new species
<220> FEATURE:
<221> NAME/KEY: misc_feature
<222> LOCATION: (3)..(3)
<223> OTHER INFORMATION: n=a, c, g or t
<220> FEATURE:
<221> NAME/KEY: misc_feature
<222> LOCATION: (6)..(6)
<223> OTHER INFORMATION: n=a, c, g or t
<220> FEATURE:
<221> NAME/KEY: misc_feature
<222> LOCATION: (19)..(19)
<223> OTHER INFORMATION: n=a, c, g or t
<220> FEATURE:
<221> NAME/KEY: misc_feature
<222> LOCATION: (21)..(21)
<223> OTHER INFORMATION: n=a, c, g or t
<220> FEATURE:
<221> NAME/KEY: misc_feature
<222> LOCATION: (25)..(26)
<223> OTHER INFORMATION: n=a, c, g or t
<220> FEATURE:
<221> NAME/KEY: misc_feature
<222> LOCATION: (28)..(28)
<223> OTHER INFORMATION: n=a, c, g or t
<220> FEATURE:
<221> NAME/KEY: misc_feature
<222> LOCATION: (36)..(36)
<223> OTHER INFORMATION: n=a, c, g or t
<220> FEATURE:
<221> NAME/KEY: misc_feature
<222> LOCATION: (39)..(39)
<223> OTHER INFORMATION: n=a, c, g or t
<220> FEATURE:
<221> NAME/KEY: misc_feature
<222> LOCATION: (48)..(48)
<223> OTHER INFORMATION: n=a, c, g or t
<220> FEATURE:
<221> NAME/KEY: misc_feature
<222> LOCATION: (52)..(52)
<223> OTHER INFORMATION: n=a, c, g or t
<220> FEATURE:
<221> NAME/KEY: misc_feature
<222> LOCATION: (61)..(61)
<223> OTHER INFORMATION: n=a, c, g or t
<220> FEATURE:
<221> NAME/KEY: misc_feature
<222> LOCATION: (63)..(63)
<223> OTHER INFORMATION: n=a, c, g or t
<220> FEATURE:
<221> NAME/KEY: misc_feature
<222> LOCATION: (74)..(74)
<223> OTHER INFORMATION: n=a, c, g or t
<220> FEATURE:
<221> NAME/KEY: misc_feature
<222> LOCATION: (88)..(88)
<223> OTHER INFORMATION: n=a, c, g or t
<220> FEATURE:
<221> NAME/KEY: misc_feature
<222> LOCATION: (368)..(368)
<223> OTHER INFORMATION: n=a, c, g or t
<220> FEATURE:
<221> NAME/KEY: misc_feature
<222> LOCATION: (904)..(904)
<223> OTHER INFORMATION: n=a, c, g or t
<220> FEATURE:
<221> NAME/KEY: misc_feature
<222> LOCATION: (906)..(906)
<223> OTHER INFORMATION: n=a, c, g or t

<400> SEQUENCE: 11

```
ttnagngttt gatcctggnt naggnngnaa ggtggnggng tgcctaanaa angcaagttg      60
ngnggtaggg gtgntccctt agggagncc ccctggagcg gcggacgggt gagtaacacg     120
gtaggcaacy tgcctgtaag accgggataa ctaccggaaa cggtagctaa gaccggatag    180
gtgattttc cgcatggagg gatcaagaaa cacggtgcaa gctgtggctt acagatgggc     240
ctgyggcgca twagytagtt ggtggggtaa cggctcacca aggcgacgat gcgtagccga    300
cctgagaggg tgatcggcca cactgggact gagacacggc ccagactcct acggaggca     360
gcagtagngg aatcttccsc aatggacgca agtctgacgg agcaacgccg cgtgagtgaa    420
gaaggttttc ggatcgtaaa gctctgttgc caaggaagaa cgccttgggg agtcactgcc    480
ctgagggtga cggtacttga aagaaagcc ccggctaayt acgtgccagc agccgcggta     540
atacgtaggg ggcaagcgtt gtccggaatt attgggcgta aagcgcgcgc aggcggccgc    600
ttaagtttgg tgtttaagcc cggggctcaa ccccggatcg caccgaaaac tgggtggctt    660
gagtgcagga gaggaaagcg gaattccacg tgtagcggtg aaatgcgtag agatgtggag    720
gaacaccagt ggcgaaggcg ctttctggac tgtaactga cgctgaggcg cgaaagcgtg     780
gggagcaaac aggattagat accctggtag tccacgccgt aaacgatgag tgctaggtgt    840
tagggtttc gatacccttg gtgccgaagt caacacaata agcactccgc ctgtgrragt     900
acgntngcaa gagtgaaact caaaggaatt gacgggacc cgcacaagca gtggagtatg    960
tggtttaatt cgaagcaacg cgaagaacct taccaggtct tgacatccct ctgaccggta  1020
```

| | | | | |
|---|---|---|---|---|
| cagagatgta | cctttccttc | gggacagagg | agacaggtgg | tgcatggttg tcgtcagctc | 1080 |
| gtgtcgtgag | atgttgggtt | aagtcccgca | acgagcgcaa | cccttgagct tagttgccag | 1140 |
| cattaagttg | ggcactctaa | gttgactgcc | ggtgacaaac | cggaggaagg tggggatgac | 1200 |
| gtcaaatcat | catgcccctt | atgacytggg | ctacacacgt | actacaatgg ccggtacaac | 1260 |
| gggaagcgaa | ggagcgatcc | ggagcgaatc | cttataagcc | ggtctcagtt cggattgcag | 1320 |
| gctgcaactc | gcctgcatga | agtcggaatt | gctagtaatc | gcggatcagc atgccgcggt | 1380 |
| gaatacgttc | ccgggtcttg | tacacaccgc | ccgtcacacc | acgagagttt acaacacccg | 1440 |
| aagtcggtgg | ggtaaccgca | aggagccagc | cgccgaaggt | ggggtagatg attggggtga | 1500 |
| agtcgtaaca | aggtcagccg | tatcggaagg | tgcggctgga | tcacctcctt aaaa | 1554 |